United States Patent
Firlik et al.

(10) Patent No.: US 7,236,831 B2
(45) Date of Patent: Jun. 26, 2007

(54) METHODS AND APPARATUS FOR EFFECTUATING A LASTING CHANGE IN A NEURAL-FUNCTION OF A PATIENT

(75) Inventors: Andrew D. Firlik, New Canaan, CT (US); Jeffrey Balzer, Allison Park, PA (US); Bradford Evan Gliner, Sammamish, WA (US)

(73) Assignee: Northstar Neuroscience, Inc., Seattle, WA (US)

( * ) Notice: Subject to any disclaimer, the term of this patent is extended or adjusted under 35 U.S.C. 154(b) by 496 days.

(21) Appl. No.: 10/410,526

(22) Filed: Apr. 8, 2003

(65) Prior Publication Data

US 2004/0073270 A1  Apr. 15, 2004

Related U.S. Application Data

(63) Continuation-in-part of application No. 10/260,720, filed on Sep. 27, 2002, which is a continuation-in-part of application No. 09/802,808, filed on Mar. 8, 2001, now Pat. No. 7,010,351.

(60) Provisional application No. 60/325,872, filed on Sep. 28, 2001, provisional application No. 60/217,981, filed on Jul. 31, 2000.

(51) Int. Cl.
*A61N 1/00* (2006.01)
(52) U.S. Cl. .................................................... 607/45
(58) Field of Classification Search ............ 607/45, 607/48
See application file for complete search history.

(56) References Cited

U.S. PATENT DOCUMENTS

| | | | |
|---|---|---|---|
| 2,716,226 A | 8/1955 | Jonas |
| 2,721,316 A | 10/1955 | Shaw |
| 3,628,193 A | 12/1971 | Collins |
| 3,650,276 A | 3/1972 | Burghele et al. |
| 3,918,461 A | 11/1975 | Cooper |
| 4,030,509 A | 6/1977 | Heilman et al. |

(Continued)

FOREIGN PATENT DOCUMENTS

DE  19750043 A1  5/1999

(Continued)

OTHER PUBLICATIONS

U.S. Appl. No. 60/325,872, filed Sep. 28, 2001, Sheffield.

(Continued)

*Primary Examiner*—George Manuel
(74) *Attorney, Agent, or Firm*—Perkins Coie LLP

(57) ABSTRACT

The present disclosure suggests methods of selecting a stimulation site for stimulating a patient's brain or methods of effectuating a neural-function of a patient associated with an impaired body function. In one exemplary implementation, such a neural function may be effectuated by selecting a stimulation site, positioning at least a first electrode at the stimulation site, and applying an electrical potential to pass a current through the first electrode. If one aspect, this stimulation site may be selected by a) identifying a second body function that is a corollary to the impaired body function, and b) determining a corollary location of the patient's brain that is associated with the second body function and is ipsilateral to the impaired body function.

4 Claims, 9 Drawing Sheets

U.S. PATENT DOCUMENTS

| | | |
|---|---|---|
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Arseneault et al. |
| 4,308,868 A | 1/1982 | Jhabvala |
| 4,328,813 A | 5/1982 | Ray |
| 4,340,038 A | 7/1982 | McKean |
| 4,431,000 A | 2/1984 | Butler et al. |
| 4,474,186 A | 10/1984 | Ledley et al. |
| 4,542,752 A | 9/1985 | DeHaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,844,075 A | 7/1989 | Liss et al. |
| 4,865,048 A | 9/1989 | Eckerson |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |
| 5,054,906 A | 10/1991 | Lyons |
| 5,063,932 A | 11/1991 | Dahl et al. |
| 5,092,835 A | 3/1992 | Schurig et al. |
| 5,121,754 A | 6/1992 | Mullett |
| 5,143,089 A | 9/1992 | Alt |
| 5,169,384 A | 12/1992 | Bosniak et al. |
| 5,184,620 A | 2/1993 | Cudahy et al. |
| 5,193,540 A | 3/1993 | Schulman et al. |
| 5,215,086 A | 6/1993 | Terry, Jr. et al. |
| 5,224,491 A | 7/1993 | Mehra |
| 5,255,678 A | 10/1993 | Deslauriers |
| 5,263,967 A | 11/1993 | Lyons |
| 5,271,417 A | 12/1993 | Swanson et al. |
| 5,282,468 A | 2/1994 | Klepinski |
| 5,299,569 A | 4/1994 | Wernicke et al. |
| 5,303,705 A | 4/1994 | Nenov |
| 5,304,206 A | 4/1994 | Baker, Jr. et al. |
| 5,314,458 A | 5/1994 | Najafi et al. |
| 5,358,513 A | 10/1994 | Powell, III et al. |
| 5,370,672 A | 12/1994 | Fowler et al. |
| 5,405,375 A | 4/1995 | Ayers et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,464,446 A | 11/1995 | Dreessen et al. |
| 5,520,190 A | 5/1996 | Benedict et al. |
| 5,522,864 A | 6/1996 | Wallace et al. |
| 5,537,512 A | 7/1996 | Hsia et al. |
| 5,540,736 A | 7/1996 | Haimovish et al. |
| 5,549,655 A | 8/1996 | Erickson |
| 5,562,708 A | 10/1996 | Combs et al. |
| 5,575,813 A | 11/1996 | Edell et al. |
| 5,591,216 A | 1/1997 | Testerman et al. |
| 5,593,432 A | 1/1997 | Crowther et al. |
| 5,601,611 A | 2/1997 | Fayram et al. |
| 5,611,350 A | 3/1997 | John |
| 5,618,531 A | 4/1997 | Cherksey |
| 5,628,317 A | 5/1997 | Starkebaum et al. |
| 5,674,251 A | 10/1997 | Combs et al. |
| 5,676,655 A | 10/1997 | Howard, III et al. |
| 5,683,422 A | 11/1997 | Rise |
| 5,702,429 A | 12/1997 | King |
| 5,707,334 A | 1/1998 | Young |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski et al. |
| 5,735,814 A | 4/1998 | Elsberry et al. |
| 5,750,376 A | 5/1998 | Weiss et al. |
| 5,752,979 A | 5/1998 | Benabid |
| 5,769,778 A | 6/1998 | Abrams et al. |
| 5,772,591 A | 6/1998 | Cram |
| 5,782,798 A | 7/1998 | Rise |
| 5,782,873 A | 7/1998 | Collins |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,709 A | 11/1998 | Rise et al. |
| 5,843,148 A | 12/1998 | Gijsbers et al. |
| 5,843,150 A | 12/1998 | Dreessen et al. |
| 5,865,842 A | 2/1999 | Knuth et al. |
| 5,871,517 A | 2/1999 | Abrams et al. |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsch |
| 5,913,882 A | 6/1999 | King |
| 5,916,171 A | 6/1999 | Mayevsky |
| 5,925,070 A | 7/1999 | King et al. |
| 5,938,688 A | 8/1999 | Schiff |
| 5,938,689 A | 8/1999 | Fischell et al. |
| 5,941,906 A | 8/1999 | Barreras, Sr. et al. |
| 5,964,794 A | 10/1999 | Bolz et al. |
| 5,975,085 A | 11/1999 | Rise |
| 5,978,702 A | 11/1999 | Ward et al. |
| 5,983,140 A | 11/1999 | Smith et al. |
| 6,006,124 A | 12/1999 | Fischell et al. |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,026,326 A | 2/2000 | Bardy |
| 6,035,236 A | 3/2000 | Jarding et al. |
| 6,040,180 A | 3/2000 | Johe |
| 6,042,579 A | 3/2000 | Elsberry et al. |
| 6,052,624 A | 4/2000 | Mann |
| 6,055,456 A | 4/2000 | Gerber |
| 6,057,846 A | 5/2000 | Sever, Jr. |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,095,148 A | 8/2000 | Shastri et al. |
| 6,104,956 A * | 8/2000 | Naritoku et al. .............. 607/45 |
| 6,104,960 A | 8/2000 | Duysens et al. |
| 6,122,548 A | 9/2000 | Starkebaum et al. |
| 6,126,657 A | 10/2000 | Edwards et al. |
| 6,128,537 A | 10/2000 | Rise |
| 6,128,538 A | 10/2000 | Fischell et al. |
| 6,134,474 A | 10/2000 | Fischell et al. |
| 6,152,143 A | 11/2000 | Edwards |
| 6,161,044 A | 12/2000 | Silverstone |
| 6,161,045 A * | 12/2000 | Fischell et al. .............. 607/45 |
| 6,176,242 B1 | 1/2001 | Rise |
| 6,190,893 B1 | 2/2001 | Shastri et al. |
| 6,198,958 B1 | 3/2001 | Ives et al. |
| 6,205,360 B1 | 3/2001 | Carter et al. |
| 6,210,417 B1 | 4/2001 | Baudino et al. |
| 6,221,908 B1 | 4/2001 | Kilgard et al. |
| 6,230,049 B1 | 5/2001 | Fischell et al. |
| 6,236,892 B1 | 5/2001 | Feler |
| 6,246,912 B1 | 6/2001 | Sluijter et al. |
| 6,280,462 B1 | 8/2001 | Hauser et al. |
| 6,301,493 B1 | 10/2001 | Marro et al. |
| 6,319,241 B1 | 11/2001 | King et al. |
| 6,339,725 B1 | 1/2002 | Naritoku et al. |
| 6,353,754 B1 | 3/2002 | Fischell et al. |
| 6,354,299 B1 | 3/2002 | Fischell et al. |

| | | |
|---|---|---|
| 6,356,792 B1 | 3/2002 | Errico |
| 6,360,122 B1 | 3/2002 | Fischell et al. |
| 6,366,813 B1 | 4/2002 | DiLorenzo |
| 6,375,666 B1 | 4/2002 | Mische |
| 6,405,079 B1 | 6/2002 | Ansarinia |
| 6,418,344 B1 | 7/2002 | Rezai et al. |
| 6,427,086 B1 | 7/2002 | Fischell et al. |
| 6,456,886 B1 | 9/2002 | Howard, III et al. |
| 6,459,936 B2 | 10/2002 | Fischell et al. |
| 6,463,328 B1 | 10/2002 | John |
| 6,464,356 B1 | 10/2002 | Sabel |
| 6,466,822 B1 | 10/2002 | Pless |
| 6,473,568 B2 | 10/2002 | Kashiyama |
| 6,473,639 B1 | 10/2002 | Fischell et al. |
| 6,480,743 B1 | 11/2002 | Kirkpatrick et al. |
| 6,484,059 B2 | 11/2002 | Gielen |
| 6,487,450 B1 | 11/2002 | Chen |
| 6,499,488 B1 | 12/2002 | Hunter et al. |
| 6,505,075 B1 | 1/2003 | Weiner |
| 6,507,755 B1 | 1/2003 | Gozani et al. |
| 6,529,774 B1 | 3/2003 | Greene |
| 6,539,263 B1 | 3/2003 | Schiff et al. |
| 6,556,868 B2 | 4/2003 | Naritoku et al. |
| 6,569,654 B2 | 5/2003 | Shastri et al. |
| 6,591,138 B1 | 7/2003 | Fischell et al. |
| 6,597,954 B1 * | 7/2003 | Pless et al. .................... 607/62 |
| 6,615,065 B1 | 9/2003 | Barrett et al. |
| 6,622,048 B1 | 9/2003 | Mann |
| 6,633,780 B1 | 10/2003 | Berger |
| 6,665,562 B2 | 12/2003 | Gluckman et al. |
| 6,684,105 B2 | 1/2004 | Cohen et al. |
| 6,687,525 B2 | 2/2004 | Llinas |
| 6,690,974 B2 | 2/2004 | Archer et al. |
| 6,708,064 B2 | 3/2004 | Rezai |
| 6,725,094 B2 | 4/2004 | Saberski |
| 6,764,498 B2 | 7/2004 | Mische |
| 6,782,292 B2 | 8/2004 | Whitehurst |
| 6,788,975 B1 | 9/2004 | Whitehurst et al. |
| 6,795,737 B2 | 9/2004 | Gielen et al. |
| 6,810,286 B2 | 10/2004 | Donovan et al. |
| 6,839,594 B2 | 1/2005 | Cohen et al. |
| 6,873,872 B2 | 3/2005 | Gluckman et al. |
| 6,892,097 B2 | 5/2005 | Holsheimer |
| 6,895,280 B2 | 5/2005 | Meadows et al. |
| 6,907,296 B1 | 6/2005 | Doan et al. |
| 6,934,580 B1 * | 8/2005 | Osorio et al. ............... 600/545 |
| 6,944,497 B2 | 9/2005 | Stypulkowski |
| 6,944,501 B1 | 9/2005 | Pless |
| 6,959,215 B2 | 10/2005 | Gliner et al. |
| 6,990,377 B2 | 1/2006 | Gliner et al. |
| 7,006,859 B1 | 2/2006 | Osorio et al. |
| 7,010,351 B2 | 3/2006 | Firlik et al. |
| 7,024,247 B2 | 4/2006 | Gliner et al. |
| 7,107,097 B2 | 9/2006 | Stern et al. |
| 7,110,820 B2 | 9/2006 | Tcheng et al. |
| 2002/0028072 A1 | 3/2002 | Kashiyama |
| 2002/0077670 A1 | 6/2002 | Archer |
| 2002/0087201 A1 | 7/2002 | Firlik |
| 2002/0091419 A1 | 7/2002 | Firlik |
| 2002/0099412 A1 | 7/2002 | Fischell et al. |
| 2002/0169485 A1 | 11/2002 | Pless et al. |
| 2003/0074032 A1 | 4/2003 | Gliner |
| 2003/0078633 A1 | 4/2003 | Firlik et al. |
| 2003/0088274 A1 | 5/2003 | Gliner et al. |
| 2003/0097161 A1 | 5/2003 | Firlik et al. |
| 2003/0114886 A1 | 6/2003 | Gluckman et al. |
| 2003/0125772 A1 | 7/2003 | Olson et al. |
| 2003/0125786 A1 | 7/2003 | Gliner et al. |
| 2003/0130706 A1 | 7/2003 | Sheffield et al. |
| 2003/0138550 A1 | 7/2003 | Salaam |
| 2003/0149457 A1 | 8/2003 | Tcheng et al. |
| 2003/0176901 A1 | 9/2003 | May |
| 2003/0187490 A1 | 10/2003 | Gliner |
| 2003/0187491 A1 | 10/2003 | Greenberg et al. |
| 2004/0073270 A1 | 4/2004 | Firlik et al. |
| 2004/0082847 A1 | 4/2004 | McDermott |
| 2004/0088024 A1 | 5/2004 | Firlik et al. |
| 2004/0092809 A1 | 5/2004 | DeCharms |
| 2004/0102828 A1 | 5/2004 | Lowry et al. |
| 2004/0111127 A1 | 6/2004 | Gliner et al. |
| 2004/0131998 A1 | 7/2004 | Marom et al. |
| 2004/0138550 A1 | 7/2004 | Hartlep et al. |
| 2004/0158298 A1 | 8/2004 | Gliner |
| 2004/0176831 A1 | 9/2004 | Gliner et al. |
| 2004/0181263 A1 | 9/2004 | Balzer et al. |
| 2004/0215287 A1 | 10/2004 | Swoyer et al. |
| 2004/0236388 A1 | 11/2004 | Gielen et al. |
| 2004/0243205 A1 | 12/2004 | Keravel et al. |
| 2004/0249422 A1 | 12/2004 | Gliner et al. |
| 2005/0004620 A1 | 1/2005 | Singhal et al. |
| 2005/0015129 A1 | 1/2005 | Mische |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2005/0182453 A1 | 8/2005 | Whitehurst |
| 2006/0015153 A1 | 1/2006 | Gliner et al. |
| 2006/0106430 A1 | 5/2006 | Fowler et al. |
| 2006/0106431 A1 | 5/2006 | Wyler et al. |
| 2006/0129205 A1 | 6/2006 | Boveja et al. |
| 2006/0173522 A1 | 8/2006 | Osorio |
| 2006/0217782 A1 | 9/2006 | Boveja et al. |

FOREIGN PATENT DOCUMENTS

| | | |
|---|---|---|
| EP | 0214527 | 3/1987 |
| EP | 0319844 A1 | 6/1989 |
| EP | 0 998 958 A2 | 10/2000 |
| EP | 1145736 | 10/2001 |
| EP | 1180056 | 11/2003 |
| WO | WO 87/07511 | 12/1987 |
| WO | WO-94/07564 | 4/1994 |
| WO | WO 95/21591 | 8/1995 |
| WO | WO 98/06342 | 2/1998 |
| WO | WO 01/97906 | 12/2001 |
| WO | WO 02/09811 | 2/2002 |
| WO | WO 02/36003 | 5/2002 |
| WO | WO 02/38031 | 5/2002 |
| WO | WO 02/38217 | 5/2002 |
| WO | WO-03/082402 | 3/2003 |
| WO | WO-03/043690 | 5/2003 |

OTHER PUBLICATIONS

U.S. Appl. No. 60/325,978, filed Sep. 28, 2001, Gliner.
U.S. Appl. No. 10/072,700, filed Feb. 7, 2002, Firlik.
U.S. Appl. No. 09/978,134, filed Oct. 15, 2001, Gliner.
Siebner et al., "Lasting cortical activation after repetitive TMS of the motor cortex," NEUROLOGY 54, pp. 956-963 (Feb. 2000).
Ziemann et al., "Modulation of Plasticity in Human Motor Cortex after Forearm Ischemic Nerve Block," The Journal of Neuroscience, vol. 18, No. 3, pp. 1115-1123 (Feb. 1998).
Oliveri et al., "Paired transcranial magnetic stimulation protocols reveal a pattern of inhibition and facilitation in the human parietal cortex," The Journal of Physiology, 529.2, pp. 461-468 (2000).

Classen, et al., "Rapid Plasticity of Human Cortical Movement Representation Induced by Practice," The Journal of Neurophysiology, vol. 79, No. 2, pp. 1117-1123 (Feb. 1998).

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Gordon et al., "Parameters for direct cortical electrical stimulation in the human: histopathologic confirmation," Electroencephalography and clinical Neurophysiology, vol. 75, pp. 371-377 (1990).

Cramer, S.C. and Bastings, E.P., "Mapping clinically relevant plasticity after stroke," Neuropharmacology vol. 19, No. 5, pp. 842-851 (Apr. 2000).

Hodge, Jr., C.J. and Boakye, M., "Biological Plasticity: The Future of Science in Neurosurgery," Neurosurgery, vol. 48, No. 1 (Jan. 2001).

Nitsche, M.A. and Paulus, W., "Excitability changes induced in the human motor cortex by weak transcranial direct current stimulation," The Journal of Physiology, vol. 527.3, pp. 663-639 (2000).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Cincotta et al., "Reorganization of the motor cortex in a patient with congenital hemiparesis and mirror movements," Neurology, vol. 55, pp. 129-131 (2000).

Stefan et al., "Introduction of plasticity in the human motor cortex by paired associative stimulation," Brian, vol. 123, No. 3, pp. 575-584 (Mar. 2000).

Feys et al., "Value of somatosensory and motor evoked potentials in predicting arm recovery after a stroke," (Oct. 1999).

Turton, A. and Lemon, R.N., "The contribution of fast corticospinal input to the voluntary activation of proximal muscles in normal subjects and in stroke patients," Exp. Brain Res., vol. 129, pp. 559-572 (1999).

Martinez et al., "Motor hand recovery after stroke Prognostic yield of early transcranial magnetic stimulation," Electromyography. Clin. Neurophysiology, vol. 39, pp. 405-410 (1999).

Saitou et al., "Cerebral Blood volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Sanes, J.N. and Donoghue, J.P., "Plasticity and Primary Motor Cortex," Annu. Rev. Neurosci. 23:393-415 (2000).

Franzini et al., "Reversal of thalamic hand syndrome by long-term motor cortex stimulation," Journal of Neurosurgery 93:873-875 (2000).

Walker-Batson et al., "Amphetamine Paired With Physical Therapy Accelerates Motor Recovery After Stroke," Stroke, vol. 26, No. 12, pp. 2254-2259 (1995).

Netz et al., "Reorganization of motor output in the non-affected hemisphere after stroke," Brain, 120, pp. 1579-1586 (1997).

Sanes, "The relation between Human Brain Activity and Hand Movements," Neuroimage 11, pp. 370-374 (2000).

Sanes, J. and Donoghue, J.P., "Plasticity and Primary Motor Cortex," Annual Review of Neuroscience 23:393-415 (2000).

Sandkühler, "Learning and memory in pain pathways," Pain 88, pp. 113-118 (2000).

Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).

Bel, S. and Bauer, B.L., "Dorsal Column Stimulation (DCS): Cost to Benefit Analysis," Acta Neurochirurgica, Suppl. 52, pp. 121-123 (1991).

Kopell et al., "The Continuing Evolution of Psychiatric Neurosurgery," CNS Spectrums, vol. 5, No. 10, pp. 20-31 (Oct. 2000).

Rezai, "Neurostimulation," Neurological Research, vol. 22, No. 3 pp. 235-273 (Apr. 2000).

Turton et al., "Contralateral and ipsilateral EMG responses to transcranial magnetic stimulation during recovery of arm and hand function after stroke," Electroencephalography and Clinical Neurophysiology 101 pp. 316-328 (1996).

Bütefisch et al., "Mechanisms of use-dependent plasticity in the human motor cortex," Proc. Natl. Acad. Sci. USA, vol. 97, No. 7, pp. 3661-3665 (Mar. 2000).

Van Der Lee et al., "Intra—and Interrater Reliability of the Action Research Arm Test: A Practical Test of Upper Extremity Function in Patients With Stroke," Arch. Phys. Med. Rehabil., vol. 82 pp. 14-19 (Jan. 2001).

Kauhanen et al., "Domans and Determinants of Quality of Life After Stroke Caused by Brian Infarction," Arch. Phys. Med. Rehabil., vol. 81, pp. 1541-1546 (Dec. 2000).

Ziemann et al., "Modulation of Plasticity in Human Motor Cortex after Forearm Ischemic Nerve Block," The Journal of Neuroscience 18(3): 1115-1123 (Feb. 1998).

Roux et al., "Chronic Motor Cortex Stimulation for Phantom Limb Pain: A Functional Magnetic Resonance Imagining Study: Technical Cast Report," Neurosurgery, vol. 49, No. 3 (Mar. 2001).

Cohen et al., "Studies of Neuroplasticity With Transcranial Magnetic Stimulation," The Journal of Clinical Neurophysiology, vol. 15, No. 4 (1998).

Shimizu et al., "Therapeutic efficacy of transcranial magnetic stimulation for hereditary spinocerebellar degeneration," Tohoku Journal of Experimental Medicine, 189(3):203-211 (Nov. 1999).

Liepert et al., "Treatment-Induced Cortical Reorganization After Stroke in Humans," Stroke, 31:1210-1216 (2000).

Schiff et al., "A neuromodulation strategy for rational therapy of complex brain injury states," Neurological Research, vol. 22 pp. 267-272 (Apr. 2000).

Gladstone et al., "Enhancing Recovery after Stroke with Noradrenergic Pharmacotherapy: A New Frontier?," Can J. Neurol. Sci., vol. 27, No. 2 (May 2000).

Pascual-Leone et al., "Study and Modulation of Human Cortical Excitability With Transcranial Magnetic Stimulation," Journal of Clinical Neurophysiology, vol. 15, No. 4 (1998).

Pascual-Leone et al., "Transcranial magnetic stimulation and neuroplasticity," Neurophycologia 37, pp. 207-217 (1999).

Stefan et al., "Induction of plasticity in the human motor cortex by paired associative stimulation," Brain, 123, pp. 572-584 (2000).

Canavero, S. and Paolotti, R., "Extradural Motor Cortex Stimulation for Advanced Parkinson's Disease: Case Report," *Movement Disorders 15(1)*: 169-171, 2000.

International Search Report for Application No. PCT/US02/32695; Applicant: Vertis Neuroscience, Inc.; Dec. 27, 2002; 9 pgs; European Patent Office.

International Search Report for Application No. PCT/US02/07077; Applicant: Vertis Neuroscience, Inc.; Oct. 22, 2002; 7 pgs; European Patent Office.

Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).

Behrens, T. et al., "Non-invasive mapping of connections between human thalamus and cortex using diffusion imaging." Nature Neuroscience, vol. 6 No. 7, pp. 750-757 (Jul. 2003).

Benabid, A.L. et al, "Chronic electrical stimulation of the ventralis intermedius nucleus of the thalamus as a treatment of movement disorders," J. Neurosurg., Apr. 1997, 86(4); 737; http://www.ncbi.nlm.nih.gov; [Nov. 18, 2003].

Brain Electrical Stimulation to Enhance Recovery After Stroke. ClinicalTrials.gov. [Retrieved on Dec. 22, 2005]. Retrieved from the internet <URL http://www.clinicaltrials.gov/ct/show/NCT00085657?order=2>.

Burnett, Mark G. et al., "Diffuse optical measurement of blood flow, blood oxygenation, and metabolism in a human brain during sensorimotor cortex activation," Optics Letters, vol. 29, No. 15, pp: 1766-1768 (Aug. 1, 2004).

Cytokines Web Clinical Significance. Cytokines Web, 2 pages. [Retrieved on Sep. 2, 2005]. Retrieved from the internet: <URL: <http://cmbi.bjmu.edu.cn/cmbidata/cgf/CGF_Database/cytweb/roles/index.html>>.

De Ridder, Dirk et al., "Magnetic and electrical stimulation of the auditory cortex for intractable tinnitus," Journal Neurosurg., vol. 100, pp. 560-564, (Mar. 2004).

Di Lazzaro, V. et al., "Theta-burst repetitive transcranial magnetic stimulation suppressess specific excitatory circuits in the human motor cortex," Physiology in Press; published online on Apr. 21, 2005 as 10.1113/jphysio.2005.087288.

Ding, Yuemin et al., "Neural Plasticity After Spinal Cord Injury," Current Pharmaceutical Design vol. 11, pp. 1441-1450, Abstract Only—1 page (Apr. 2005).

Duncan, Pamela W. et al., "Defining post-stroke recovery: implications for design and interpretation of drug trials," Neuropharmacology vol. 39, pp. 835-841 (2000).

Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).

Hagemann, Georg et al., "Increased Long-Term Potentiation in the Surround of Experimentally Induced Focal Cortical Infarction," Annals of Neurology, vol. 44, No. 2, pp. 255-258 (Aug. 1998).

Hayakawa, Toshiji et al., "Changes in Cerebral Oxygenation and Hemodynamics During Obstructive Sleep Apneas," Chest, vol. 109, pp. 916-921 (1996).

Hoshi, Yoko et al., "Detection of dynamic changes in cerebral oxygenation coupled to neuronal function during mental work in a man," Neuroscience Letters, vol. 150, pp. 5-8 (1993).

Hoshino et al., "Application of multichannel near-infrared spectroscopic topography to physiological monitoring of the cortex during cortical mapping: technical case report," Surgical Neurology, vol. 64, pp. 272-275 (2005).

Huang, Ying-Zu et al., "Theta Burst Stimulation of the Human Motor Cortex," Neuron, vol. 45, pp. 201-206 (Jan. 20, 2005).

Hummel, Friedheim et al., "Effects of non-invasive cortical stimulation on skilled motor function in chronic stroke," Brain Advance Access, Jan. 5, 2005, pp. 1-10, Brain.

Kilgard, Michael et al., "Cortical Map Reorganization Enabled by Nucleus Basalis Activity," Science, vol. 279 pp. 1714-1717 (Mar. 13, 1998).

Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

L-DOPA dyskinesias. BioChemistry of PD. [Retrieved on Dec. 22, 2005]. Retrieved from the internet <URL <http://www.mayo.edu/fdp/pd-info/dyskinesias.htm>>.

Mansur, C.G., et al., "A sham stimulation-controlled trial of rTMS of the unaffected hemisphere in stroke patients," Neurology, vol. 64, pp. 1802-1804 (2005).

Martin et al, "Transcranial Magnetic Stimulation as a Complementary Treatment for Aphasia," Semin Speech Language, vol. 25, pp. 181-191 (2004) Abstract Only—1 page.:

Nitsche, Michael A. et al., "Level of action of cathodal DC polarisation induced inhibition of the human motor cortex," Dec. 2, 2002, Clinical Neurophysiology 114 (2003) 600-604.

Nitsche, Michael A., et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.

Panchanathan, Sethuraman et al., "Rehabilitation of patients with hemispatial neglect using visual-haptic feedback in Virtual reality environment," [Retrieved on Dec. 22, 2005]. Retrieved from the internet <URL <http://www.public.asu.edu/~tmcdani/publications.htm>>.

Paulus, W, "Supplements to clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimulation," Neuron, vol. 45, pp. 181-183 (Jan. 20, 2005).

Penn, Michael, "Stemming Parkinson's," On Wisconsin Alumni Magazine, Summer 2003, [Retrieved on Dec. 22, 2005]. Retrieved from the internet <URL http://www.uwalumni.com/onwisconsin/2003_summer/research.html>.

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

SCIRun. Scientific Computing and Imaging Institute, 2 pages. [Retrieved on Jul. 24, 2005]. Retrieved from the internet: <URL: <http://sofware.sci.utah.edu/scirun.html>>.

Strangman, Gary et al., "A Quantitative Comparison of Simultaneous BOLD fMRI and NIRS Recordings during Functional Brain Activation," NeuroImage, vol. 17, pp. 719-731 (2002).

Strangman, Gary et al., "Factors affecting the accuracy of near-infrared spectroscopy concentration calculations for focal changes in oxygenation parameters," NeuroImage, vol. 18, pp. 865-879 (2003).

Strangman, Gary et al., "Non-Invasive Neuroimaging Using Near-Infrared Light," Biological Psychiatry, vol. 52, pp. 679-693 (2002).

Strens, Lucy et al., "The ipsilateral Human Motor Cortex Can Functionally Compensate for Acute Contralateral Motor Cortex Dysfunction," Current Biology, vol. 13, pp. 1201-1205 (Jul. 15, 2003).

Taga, Gentaro et al., "Brain imaging in awake infants by near-infrared optical topogrpahy," PNAS, vol. 100, No. 19, pp. 10722-10727 (Sep. 16, 2003).

The GES 250 for Dense-Array EEG Research. Electrical Geodesics, Inc., 3 pages. [Retrieved on Aug. 25, 2005]. Retrieved from the internet: <URL: http://www.egi.com/ges250r_n.html>.

The INVOS Cerebral Oximeter. Somanetics, 1 page [Retrieved on Dec. 22, 2005]. Retrieved from the internet <URL <http://www.somanetics.net/invos.htm>>.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Toronov, Vlad et al., "Near-infrared study of fluctuations in cerebral hemodynamics during rest and motor stimulation; Temporal analysis and spatial mapping," Medical Physics, vol. 27, No. 4, pp. 801-815 (Apr. 2000).

Tractography. Absolute Astronomy Reference, 2 pages. [Retrieved on Jul. 24, 2005]. Retrieved from the internet: <URL: http://www.absoluteastronomy.com/encyclopedia/T/Tr/Tractography.htm>.

Tsubokawa, T., "Chronic Motor Cortex Stimulation in Patients with Thalamic Pain," J. Neurosurg 78:393-401, (Mar. 1993).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Weinand, Martin E. et al., "Cerebral blood flow and temporal lobe epileptogenicity," [Retrieved on Dec. 22, 2005]. Retrieved from the internet: <URL http://www.aans.org/education/journal/neurosurgical/nov96/1-5-3.asp>.

Bluestone, Avraham Y. et al., "Three-dimensional optical tomography of hemodynamics in the human head," Optics Express, vol. 9, No. 6, pp. 272-286 (Sep. 10, 2001).

Bury, Scott et al., "The Effects of Behavioral Demand on Motor Cortical and Cerebellar Structural Plasticity After Brain Injury in Adult Rats," [Retrieved on Mar. 1, 2003]. Retrieved from the internet: <URL: http://www.mcmaster.ca.inabis98/schallert/bury0827/index.html>.

Cao, Yue et al., "Cortical Language Activation in Stroke Patients Recovering From Aphasia With Functional MRI," Stroke, vol. 30, pp. 2331-2340, Nov. 1999.

How Imagent™ Works. ISS Inc., 1 page [Retrieved on Oct. 14, 2005]. Retrieved from the internet: <URL http://www.iss.com/Products/imagent_fmri.html>.

Imagent™ Functional Brain Imaging System. ISS, Inc., 2 pages [Retrieved on Oct. 14, 2005]. Retrieved from the internet: <URL http://www.iss.com/Products/imagent.html>.

Imagent™ functional Near Infrared Imaging System (fNIRS) Brain Imaging Using Infrared Photons. ISS Inc., 8 pages [Retrieved on Oct. 14, 2005]. Retrieved from the internet: <URL http://www.iss.com/products/imagent/Imagent.pdf>.

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp.: 571-577 (Dec. 2003).

Keyvani, Kathy et al., "Suppression of proteasome C2 contralateral to ischemic lesions in rat brain," Brain Research, vol. 858, pp. 386-392, 2000.

Meyerson, B.A. et al., "Motor Cortex Stimulation as Treatment of Trigeminal Neuropathic Pain," Acta Neurochirurgica Supplementum, vol. 58, pp. 150-153 (1993).

Nudo, Randolph J., et al., "Recovery after damage to motor cortical areas," Current Opinion in Neurobiology, vol. 9, Issue 6, pp. 740-747, Dec. 1, 1999.

Tang, Cha-Min et al., "Optical Coherence Tomography of the Human Basal Ganglion," 2003 Deep Brain Stimulation Consortium Meeting, Sep. 29-30, 2003, Washington DC.

Timmermann, Lars et al., "The cerebral oscillatory network of parkinsonian resting tremor," Brain, vol. 126, pp. 199-212, (2003).

Tsubokawa, T. et al., "Chronic Motor Cortex Stimulation for the Treatment of Central Pain", Acta Neurochirurgica, Suppl. 52, pp. 137-139 (1991).

Tsubokawa, T. et al., "Treatment of Thalamic Pain by Chronic Motor Cortex Stimulation," PACE, vol. 14, pp. 131-134 (Jan. 1991).

Yokoh, Arika et al., "Intermittent versus continuous brain retraction," Journal of Neurosurgery, vol. 58, pp. 918-923 (Jun. 1983).

U.S. Appl. No. 10/583,630, filed Jun. 20, 2006, Lozano.
U.S. Appl. No. 11/254,060, Oct. 19, 2005, Wyler.
U.S. Appl. No. 11/254,240, filed Oct. 19, 2005, Wyler.
U.S. Appl. No. 11/255,187, filed Oct. 19, 2005, Firlik.
U.S. Appl. No. 11/344,453, filed Jan. 30, 2006, Gllner.
U.S. Appl. No. 11/518,139, filed Sep. 7, 2006, Weinand.
U.S. Appl. No. 11/583,349, filed Oct. 18, 2006, Sloan.
U.S. Appl. No. 11/638,326, filed Dec. 12, 2006, Gilner et al.

Beveridge, J.A., "Use of Exogenous Electric Current in the Treatment of Delayed Lesions in Peripheral Nerves," Plastic and Reconstructive Surgery, Oct. 1988, vol. 82, No. 4, pp. 573-579.

Mendonca, A.C., "Directly applied low intensity direct electric current enhances peripheral nerve regeneration on rats," Journal of Neuroscience Methods, 2003, vol. 129, pp. 183-190.

Politis, M. J., "Mammalian Optic Nerve Regeneration Following the Application of Electric Fields," The Journal of Trauma, Nov. 1988, vol. 28, No. 11, pp. 1548-1552.

CNN. com, Health, "Lab Zaps Strokes with Magnetic Pulses," htt://www.cnn.com/2004/HEALTH/conditions/11/29/zapping.strokes.ap/, Nov. 29, 2004, 4 pages [Retrieved on Dec. 02, 2004].

Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).

Bezard et al., "Cortical Stimulation and Epileptic Seizure: A Study of the Potential Risk in Primates," Neurosurgery, vol. 45, No. 2, Aug. 1999, 346-350.

Binder, J. M.D., "Functional Magnetic Resonance Imaging: Language Mapping," Neurosurgery Clinics of North America, vol. 8, No. 3, Jul. 1997, pp. 383-392.

Cheun et al., "Differentiation of a Stem Cell Line Toward a Neuronal Phenotype," int. J. Devl. Neuroscience, vol. 9, No. 4, pp. 391-404 (1991).

Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.

Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.

Cramer et al., "Use of Functional MRI to Guide Decisions in a clinical Stroke Trial," Stroke, Journal of the American Heart Association, May 2005, pp. e50-e-52, American Heart Association, Dallas TX.

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.

Fregni et al., "Antiepileptic Effects of Repetitive Transcranial Magnetic Stimulation in Patients with Cortical Malformations: An EEG and Clinical Study," ASSFN Proceedings 2004, Sterotactic and Functional Neurosurgery, 2005, 83:57-62.

Haglund, Michael M. et al., "Optical imaging of epileptiform and functional activity in human cerebral cortex," Nature, Aug. 20, 1992, pp. 668-671, vol. 358, Nature Publishing Group.

Ishibashi, Tomoko et al., "Astrocytes Promote Myelination in Resonse to Electrical Impulses," Neuron 49, pp. 823-832, (Mar. 16, 2006).

Kelly-Spratt, K. "Transfection of PC-12 cells: a model system for primary neuronal cells," Qlagen News, Customer application article, www.qiagen.com, Issue 4, 1998, 2 pages.

Kimura, K. et al., "Electrically induced neurite outgrowth of PC12 cells on the electrode surface," Entrez PubMed, http://www.ncbi.nlm.nih.gov/entrez/query.fcgi?db=pubmed&cmd=Retrieve&dopt=Abstract, 1 page.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kossoff et al., "Effect of an External Responsive Neurostimulator on Seizures and Electrographic Discharges during Subdural Electrode Monitoring," Epilepsia 45(12): 1560-1567, 2004, Blackwell Publishing, Inc.

Lutsep et al., "Safety of Cortical Stimulation in Patients with Hemiparetic Stroke," Oasis, Online Abstract Submission and Invitation System-Program Planner, International Stroke Conference 2005, 1 pages, American Stroke Association.

Misawa et al., "Low-frequency transcranial magnetic stimulation for epilepsia partialis continue due to cortical dysplasia," Journal of the Neurological Sciences, vol. 234, 2005, pp. 37-39.

Motamedi et al., "Optimizing Parameters for Terminating Cortical Afterdischarges with Pulse Stimulation," Epilepsia 43(8):836-846, 2002, Blackwell Publishing, Inc.

Price, J. et al., "Neurotransplantation in neurodegenerative disease: a survey of relevant issues in developmental neurobiology," Novartis Foundation Symposium 231, 2000, pp. 148-165, Wiley, Chichester, UK.

Robinson, Kenneth R., "The Responses of Cells to Electrical Fields: A Review," The Journal of Cell Biology, vol. 101, pp. 2023-2027 (Dec. 1985).

Sioutos et al. Continuous Regional Cerebral Cortical Blood Flow Monitoring in Head-injured Patients, Neurosurgery, vol. 36, No. 5,May 1995, pp. 943-949.

The National Institutes of Health (NIH) Consensus Development Program, "Surgery for Epilepsy," National Institutes of Health Consensus Development conference Statement, Mar. 19-21, 1990, 16 pages.

Velasco et al. "Absolute and Relative Predictor Values of Som Non-Invasive and Invasive Studies for the Outcome of Anterior Temporal Lobectomy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucles; Modulation of Reticulo-Cortical Systems and Predictor Factors for Generalized Seizure control," Archives of Medical Research, vol. 31, 2000, pp. 304-315, Elsevier Science, Inc.

Velasco et al., "Electrical Stimulation for Epilepsy: Stimulation of Hippocampal foci," Stereotactic and Functional Neurosurgery, vol. 77, 2001, pp. 223-227.

Velasco et al., "Subacute and Chronic Electrical Stimulation of the Hippocampus on intractable Temporal Lobe Seizures: Preliminary Report," Archives of Medical Research, vol. 31, 2000, pp. 316-328, Elsevier Science, Inc.

Velasco et al., "Subacute Electrical Stimulation of the hippocampus Blocks Intractable Temporal Lobe Seizures and Paroxysmal EEG Activities," Epilepsia, vol. 41, No. 2, 2000, pp. 158-169, Lippincott Wilkins, Philadelphia.

Waxman et al., "The Interictal Behavior Syndrome of Temporal Lobe Epilepsy," Arch Gen Psychiagry, vol. 32, Dec. 1975, pp. 1580-1586.

Weinand et al., "Cerebral blood flow and temproal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.Org, http://www.aans.org/education/journal/neurosurgical/Nov.96/1-5-3,asp. 17 pages.

Weinand et al., Long-term ictal monitoring with subdural strip electrodes: prognostic factors for selecting temporal lobectomy canidates, J Neurosurg, vol. 77, 1992, pp. 20-28.

Weinand et al., "Surface cortical cerebral blood flow monitoring and single photon emission computed tomography: prognostic factors for selecting temportal lobectomy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005, AANS.org, http://www.aans.org/Library/Article.aspx?ArticleId=24934, 2 pages.

Woodbury, D. et al., "Adult Rat and Human Bone Marrow Stromal Cells Differentiate Into Neurons," Journal of Neuroscience Research, 2000, vol. 61, pp. 364-370, Wiley Interscience, New York, NY.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

* cited by examiner

METHODS AND APPARATUS FOR EFFECTUATING A LASTING CHANGE IN A NEURAL-FUNCTION OF A PATIENT

CROSS-REFERENCE TO RELATED APPLICATION(S)

This application is a continuation-in-part of U.S. application Ser. No. 10/260,720, filed on Sep. 27, 2002, which claims the benefit of U.S. application Ser. No. 60/325,872 filed on Sep. 28, 2001 and which is a continuation-in-part of U.S. application Ser. No. 09/802,808, filed on Mar. 8, 2001, now U.S. Pat. No. 7,010,351 which, in turn, claims the benefit of U.S. Provisional Application No. 60/217,981, filed Jul. 31, 2000. Each of these applications is incorporated by reference herein in its entirety.

TECHNICAL FIELD

Several embodiments of methods and apparatus in accordance with the invention are related to electrically stimulating a region in the cortex or other area of the brain to bring about a lasting change in a physiological function and/or a mental process of a patient.

BACKGROUND

A wide variety of mental and physical processes are controlled or influenced by neural activity in particular regions of the brain. The neural-functions in some areas of the brain (i.e., the sensory or motor cortices) are organized according to physical or cognitive functions. Several other areas of the brain also appear to have distinct functions in most individuals. In the majority of people, for example, the occipital lobes relate to vision, the left interior frontal lobes relate to language, and the cerebral cortex appears to be involved with conscious awareness, memory, and intellect.

Many problems or abnormalities can be caused by damage, disease and/or disorders in the brain. Effectively treating such abnormalities may be very difficult.

For example, a stroke is a common condition that damages the brain. Strokes are generally caused by emboli (e.g., obstruction of a vessel), hemorrhages (e.g., rupture of a vessel), or thrombi (e.g., clotting) in the vascular system of a specific region of the brain. Such events generally result in a loss or impairment of a neural function (e.g., neural functions related to facial muscles, limbs, speech, etc.). Stroke patients are typically treated using various forms of physical therapy to rehabilitate the loss of function of a limb or another affected body part. Stroke patients may also be treated using physical therapy plus an adjunctive therapy such as amphetamine treatment. For most patients, however, such treatments are minimally effective and little can be done to improve the function of an affected body part beyond the recovery that occurs naturally without intervention.

The problems or abnormalities in the brain are often related to electrical and/or chemical activity in the brain. Neural activity is governed by electrical impulses or "action potentials" generated in neurons and propagated along synaptically connected neurons. When a neuron is in a quiescent state, it is polarized negatively and exhibits a resting membrane potential typically between −70 and −60 mV. Through chemical connections known as synapses, any given neuron receives excitatory and inhibitory input signals or stimuli from other neurons. A neuron integrates the excitatory and inhibitory input signals it receives, and generates or fires a series of action potentials when the integration exceeds a threshold potential. A neural firing threshold, for example, may be approximately −55 mV.

It follows that neural activity in the brain can be influenced by electrical energy supplied from an external source such as a waveform generator. Various neural functions can be promoted or disrupted by applying an electrical current to the cortex or other region of the brain. As a result, researchers have attempted to treat physical damage, disease and disorders in the brain using electrical or magnetic stimulation signals to control or affect brain functions.

Transcranial electrical stimulation is one such approach that involves placing an electrode on the exterior of the scalp and delivering an electrical current to the brain through the scalp and skull. Another treatment approach, transcranial magnetic stimulation, involves producing a high-powered magnetic field adjacent to the exterior of the scalp over an area of the cortex. Yet another treatment approach involves direct electrical stimulation of neural tissue using implanted electrodes.

The neural stimulation signals used by these approaches may comprise a series of electrical or magnetic pulses that can affect neurons within a target neural population. Stimulation signals may be defined or described in accordance with stimulation signal parameters including pulse amplitude, pulse frequency, duty cycle, stimulation signal duration, and/or other parameters. Electrical or magnetic stimulation signals applied to a population of neurons can depolarize neurons within the population toward their threshold potentials. Depending upon stimulation signal parameters, this depolarization can cause neurons to generate or fire action potentials. Neural stimulation that elicits or induces action potentials in a functionally significant proportion of the neural population to which the stimulation is applied is referred to as supra-threshold stimulation; neural stimulation that fails to elicit action potentials in a functionally significant proportion of the neural population is defined as sub-threshold stimulation. In general, supra-threshold stimulation of a neural population triggers or activates one or more functions associated with the neural population, but sub-threshold stimulation by itself does not trigger or activate such functions. Supra-threshold neural stimulation can induce various types of measurable or monitorable responses in a patient. For example, supra-threshold stimulation applied to a patient's motor cortex can induce muscle fiber contractions in an associated part of the body.

Although electrical or magnetic stimulation of neural tissue may be directed toward producing an intended type of therapeutic, rehabilitative, or restorative neural activity, such stimulation may result in collateral neural activity. In particular, neural stimulation delivered beyond a certain intensity, period of time, level, or amplitude can give rise to seizure activity and/or other types of collateral activity. It will be appreciated that collateral neural activity may be undesirable and/or inconvenient in a neural stimulation situation.

The human brain has two hemispheres that are connected via the corpus callosum. Each hemisphere of the brain generally exerts majority control over motor functions and/or sensory functions on the opposite or "contralateral" side of the patient's body. Hence, for example, the left hemisphere of the brain has majority control over movement of the right arm and right leg. Through transcallosal connections, though, each hemisphere of the brain exerts some degree of control over the functions on the same or "ipsilateral" side of the patient's body. Hence, the right hemisphere of the brain may have some involvement in controlling movement of the right arm and right leg.

Some studies have concluded that damage to or disorders of the cerebral cortex on one hemisphere can induce long-term changes in the structure and function of a homotopic location of the contralateral hemisphere, namely a location on the undamaged cortex that is at about the same position as the position of the damaged tissue in the opposite cortex. Damage to the cortex in one hemisphere may impact the contralateral homotopic cortex in a variety of fashions, including causing increased cortical thickness, dendritic growth and/or elimination, neuronal hyperexcitability, and synaptogenesis. See, e.g., Nudo, "Recovery After Damage to Motor Cortical Areas," *Current Opinion in Neurobiology*, 1999, 9:740–747, the entirety of which is incorporated herein by reference. See also Keyvani et al., "Suppression of Proteasome C2 Contralateral to Ischemic Lesions in Rat Brain," *Brain Research* 858, (2000) 386–392.

DETAILED DESCRIPTION

Figure 1:
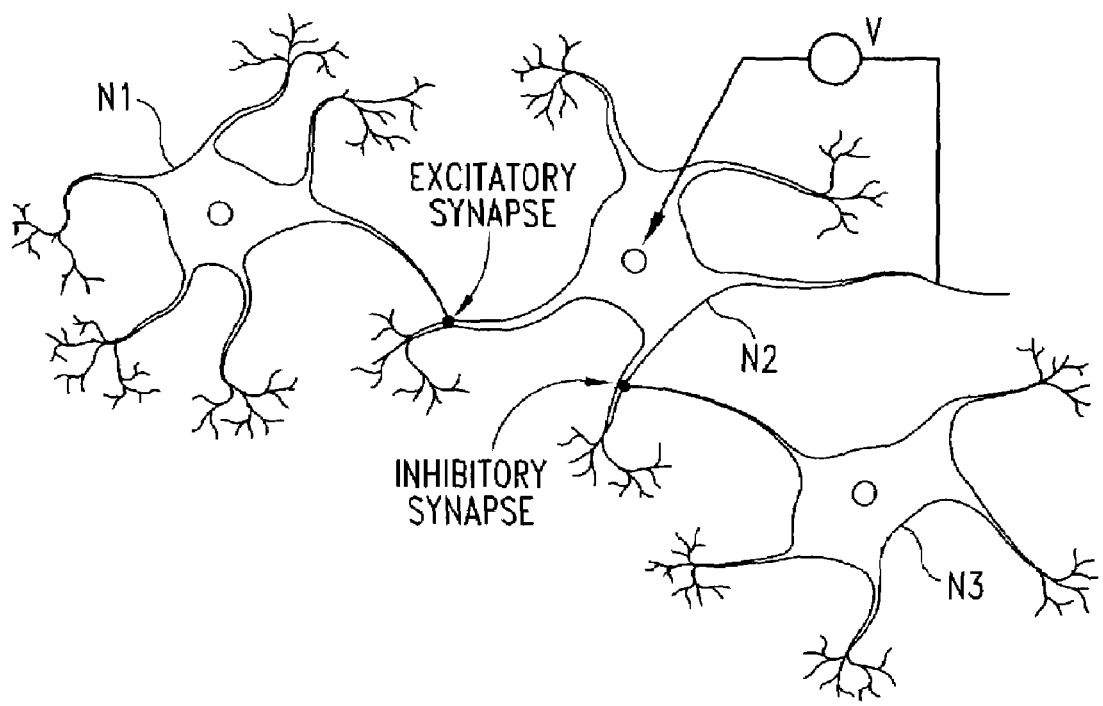
FIG. 1 is a schematic view of neurons.

The following disclosure describes several methods and apparatus for intracranial electrical stimulation to treat or otherwise effectuate a change in neural-functions of a patient. Several embodiments of methods in accordance with the invention are directed toward enhancing or otherwise inducing neuroplasticity to effectuate a particular neural-function. Neuroplasticity refers to the ability of the brain to change or adapt over time. It was once thought adult brains became relatively "hard wired" such that functionally significant neural networks could not change significantly over time or in response to injury. It has become increasingly more apparent that these neural networks can change and adapt over time so that meaningful function can be regained in response to brain injury. An aspect of several embodiments of methods in accordance with the invention is to provide the appropriate triggers for adaptive neuroplasticity. These appropriate triggers appear to cause or enable increased synchrony of functionally significant populations of neurons in a network.

Electrically enhanced or induced neural stimulation in accordance with several embodiments of the invention excites a portion of a neural network involved in a functionally significant task such that a selected population of neurons can become more strongly associated with that network. Because such a network will subserve a functionally meaningful task, such as motor relearning, the changes are more likely to be lasting because they are continually being reinforced by natural use mechanisms. The nature of stimulation in accordance with several embodiments of the invention ensures that the stimulated population of neurons links to other neurons in the functional network. It is expected that this occurs because action potentials are not actually caused by the stimulation, but rather are caused by interactions with other neurons in the network. Several aspects of the electrical stimulation in accordance with selected embodiments of the invention simply allows this to happen with an increased probability when the network is activated by favorable activities, such as rehabilitation or limb use.

The methods in accordance with the invention can be used to treat brain damage (e.g., stroke, trauma, etc.), brain disease (e.g., Alzheimer's, Pick's, Parkinson's, etc.), and/or brain disorders (e.g., epilepsy, depression, etc.). The methods in accordance with the invention can also be used to enhance functions of normal, healthy brains (e.g., learning, memory, etc.), or to control sensory functions (e.g., pain).

Certain embodiments of methods in accordance with the invention electrically stimulate the brain at a stimulation site where neuroplasticity is occurring. The stimulation site may be different than the region in the brain where neural activity is typically present to perform the particular function according to the functional organization of the brain. In one embodiment in which neuroplasticity related to the neural-function occurs in the brain, the method can include identifying the location where such neuroplasticity is present. This particular procedure may accordingly enhance a change in the neural activity to assist the brain in performing the particular neural function. In an alternative embodiment in which neuroplasticity is not occurring in the brain, an aspect is to induce neuroplasticity at a stimulation site where it is expected to occur. This particular procedure may thus induce a change in the neural activity to instigate performance of the neural function. Several embodiments of these methods are expected to produce a lasting effect on the intended neural activity at the stimulation site.

The specific details of certain embodiments of the invention are set forth in the following description and in FIGS. 1–21 to provide a thorough understanding of these embodiments to a person of ordinary skill in the art. More specifically, several embodiments of methods in accordance with the invention are initially described with reference to FIGS. 1–15, and then several embodiments of devices for stimulating the cortical and/or deep-brain regions of the brain are described with reference to FIGS. 16–21. A person skilled in the art will understand that the present invention may have additional embodiments, or that the invention can be practiced without several of the details described below.

A. Methods for Electrically Stimulating Regions of the Brain

1. Embodiments of Electrically Enhancing Neural Activity

Figure 2:
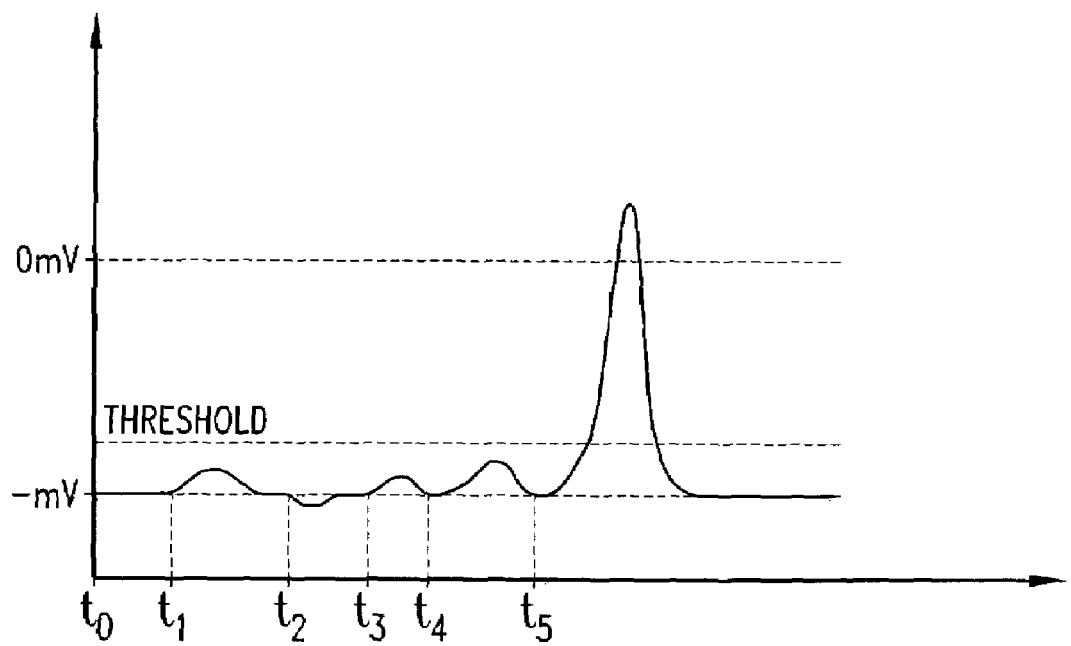
FIG. 2 is a graph illustrating firing an "action potential" associated with normal neural activity.

FIG. 1 is a schematic representation of several neurons N1–N3 and FIG. 2 is a graph illustrating an "action potential" related to neural activity in a normal neuron. Neural activity is governed by electrical impulses generated in neurons. For example, neuron N1 can send excitatory inputs to neuron N2 (e.g., times $t_1$, $t_3$ and $t_4$ in FIG. 2), and neuron N3 can send inhibitory inputs to neuron N2 (e.g., time $t_2$ in FIG. 2). The neurons receive/send excitatory and inhibitory inputs from/to a population of other neurons. The excitatory and inhibitory inputs can produce "action potentials" in the neurons, which are electrical pulses that travel through neurons by changing the flux of sodium (Na) and potassium (K) ions across the cell membrane. An action potential occurs when the resting membrane potential of the neuron surpasses a threshold level. When this threshold level is reached, an "all-or-nothing". action potential is generated. For example, as shown in FIG. 2, the excitatory input at time $t_5$ causes neuron N2 to "fire" an action potential because the input exceeds the threshold level for generating the action potential. The action potentials propagate down the length of the axon (the long process of the neuron that makes up nerves or neuronal tracts) to cause the release of neurotransmitters from that neuron that will further influence adjacent neurons.

Figure 3:
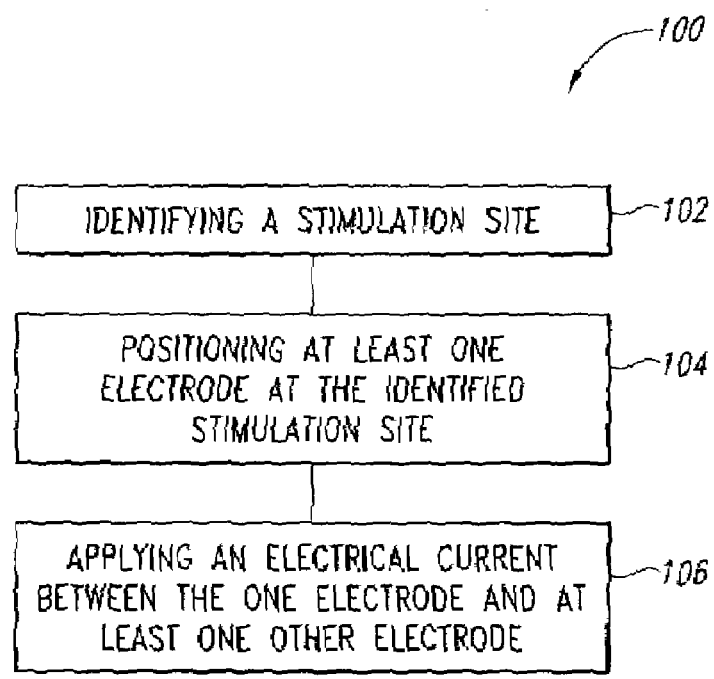
FIG. 3 is a flowchart of a method for effectuating a neural-function of a patient associated with a location in the brain in accordance with one embodiment of the invention.

FIG. 3 is a flowchart illustrating a method 100 for effectuating a neural-function in a patient in accordance with an embodiment of the invention. The neural-function, for example, can control a specific mental process or physiological function, such as a particular motor function or sensory function (e.g., movement of a limb) that is normally associated with neural activity at a "normal" location in the brain according to the functional organization of the brain. In several embodiments of the method 100, at least some neural activity related to the neural-function can be occurring at a site in the brain. The site of the neural activity may be at the normal location where neural activity typically occurs to carry out the neural-function according to the functional organization of the brain, or the site of the neural activity may be at a different location where the brain has recruited material to perform the neural activity. One aspect of several embodiments of the method 100 includes determining the location in the brain where the neural activity related to the neural-function is present. In several other embodiments of the method 100, one need not determine where the neural activity is already present. Instead, a site may be selected where the brain is likely to recruit other neurons to perform this neural activity without actually determining that the neural activity is already present at that location.

The method 100 includes a diagnostic procedure 102 involving identifying a stimulation site. In one approach, the stimulation site may be a location of the brain where an intended neural activity related to the neural-function is or is expected to be present. In another approach, the stimulation site may be a location of the brain that supports or is expected to support the intended neural-function.

The diagnostic procedure 102 may include identifying one or more exterior anatomical landmarks on the patient that correspond to such neurological regions and/or structures within the brain. The external anatomical landmarks serve as reference points for locating a structure of the brain where an intended neural activity may occur. Thus, one aspect of the diagnostic procedure 102 may include referencing the stimulation site on the brain relative to external anatomical landmarks.

More specifically, identifying an anatomical landmark may include visually determining the location of one or more reference structures (e.g., visible cranial landmarks), and locating underlying brain regions or structures (e.g., the motor strip and/or the Sylvian fissure) relative to the external location of the reference structures in a manner understood by those skilled in the art. Such reference structures may include, for example, the bregma, the midsagittal suture, and/or other well-known cranial landmarks. The methods for locating the underlying brain structure typically involve measuring distances and angles relative to the cerebral topography as known in the art of neurosurgery.

In another embodiment, the diagnostic procedure 102 includes generating the intended neural activity in the brain from a "peripheral" location that is remote from the normal location, and then determining where the intended neural activity is actually present in the brain. In an alternative embodiment, the diagnostic procedure 102 can be performed by identifying a stimulation site where neural activity has changed in response to a change in the neural-function. For example, the patient's brain may be scanned for neural activity associated with the impaired neural-function as the patient regains use of an affected limb or learns a task over a period of time. In yet another embodiment, the diagnostic procedure 102 may involve identifying a stimulation site where a corollary neural activity is present. This corollary neural activity may correspond to an unaffected or unimpaired physiological function or mental process that is a counterpart or corollary to an impaired or affected physiological function or mental process, e.g., movement of an unimpaired limb that is contralateral to an impaired homotypic limb.

The method 100 continues with an implanting procedure 104 involving positioning first and second electrodes relative to the identified stimulation site, and a stimulating procedure 106 involving applying an electrical current between the first and second electrodes. Many embodiments of the implanting procedure 104 position two or more electrodes at the stimulation site, but other embodiments of the implanting procedure involve positioning only one electrode at the stimulation site and another electrode remotely from the stimulation site. As such, the implanting procedure 104 of the method 100 can include implanting at least one electrode at the stimulation site. The procedures 102–106 are described in greater detail below.

Figure 4:
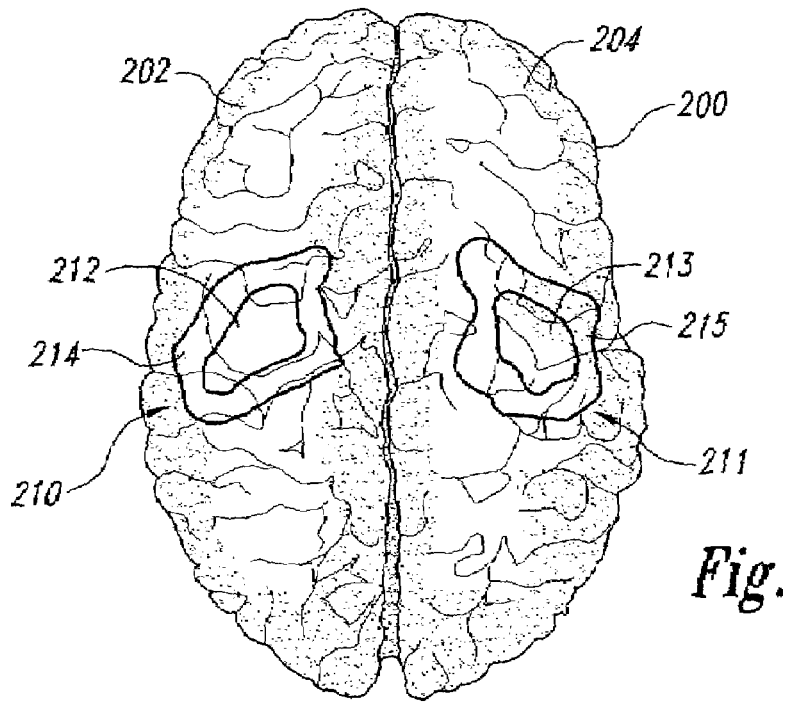
FIG. 4 is a top plan view of a portion of a brain illustrating neural activity in the brain.
Figure 5:
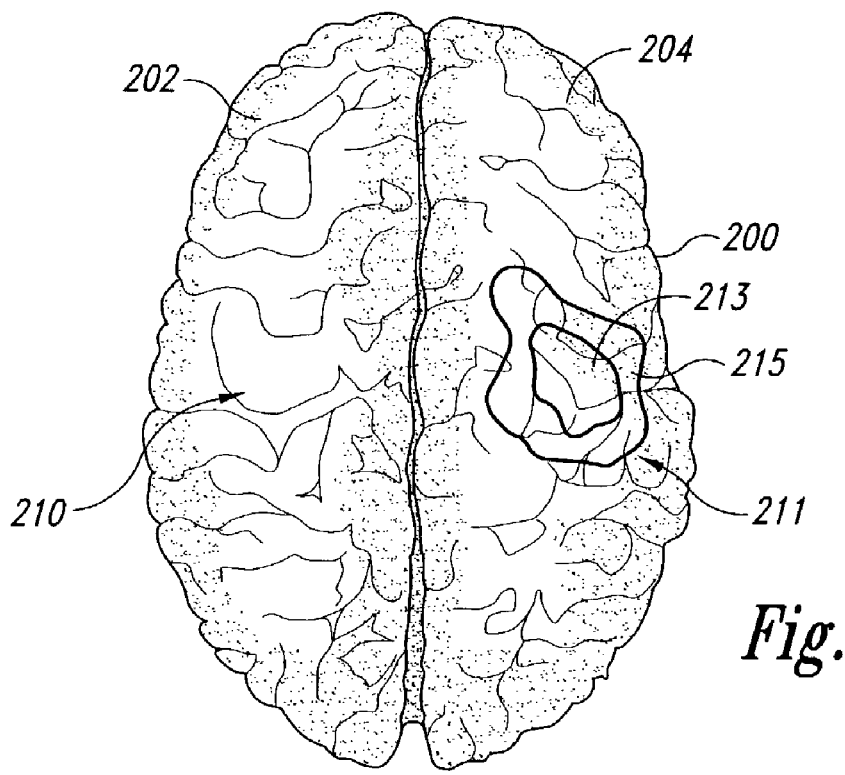
FIG. 5 is a top plan image of a portion of the brain illustrating a loss of neural activity associated with the neural-function of the patient used in one stage of a method in accordance with an embodiment of the invention.
Figure 6:
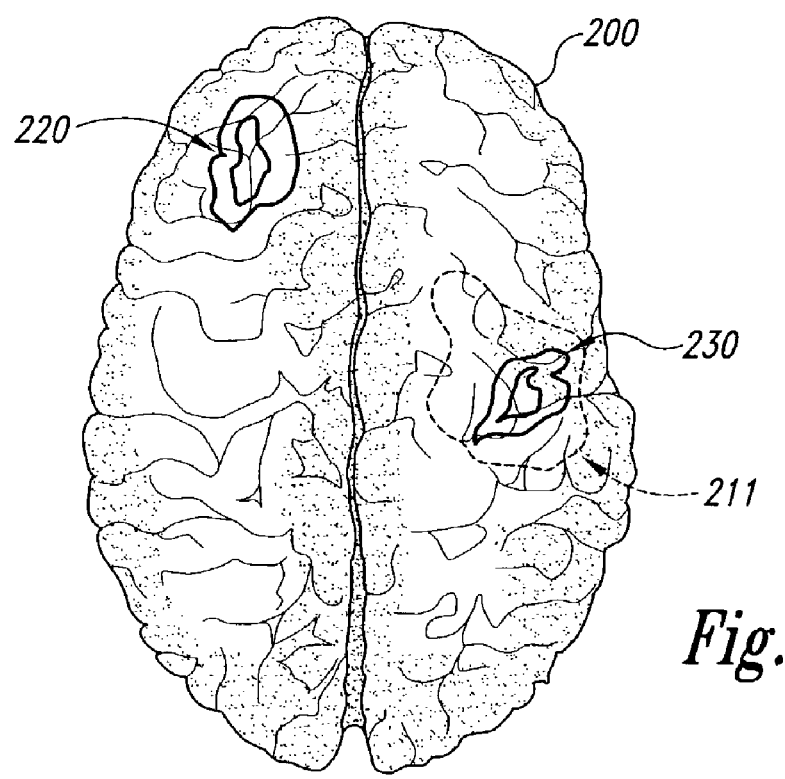
FIG. 6 is a top plan image of the brain of FIG. 3 showing a change in location of the neural activity associated with the neural-function of the patient at another stage of a method in accordance with an embodiment of the invention.

FIGS. 4–6 illustrate a specific embodiment of the diagnostic procedure 102. The diagnostic procedure 102 can be used to determine a region of the brain where stimulation will likely facilitate or effectuate the desired function, such as rehabilitating a loss of a neural-function caused by a stroke, trauma, disease or other circumstance. FIG. 4, more specifically, is an image of a normal, healthy brain 200 having a first region 210 in a first hemisphere 202 where the intended neural activity occurs to effectuate a specific neural-function in accordance with the functional organization of the brain. The first region 210 can have a high-intensity area 212 and a low-intensity area 214 in which different levels of neural activity occur. It is not necessary to obtain an image of the neural activity in the first region 210 shown in FIG. 4 to carry out the diagnostic procedure 102, but rather it is provided to show an example of neural activity that typically occurs at a "normal location" according to the functional organization of the brain 200 for a large percentage of people with normal brain function. The actual location of the first region 210 may vary somewhat between individual patients, but those skilled in the art recognize that the location of this first region 210 will bear a fairly predictable spatial relationship with respect to anatomical features of the patient's skull for a majority of individuals.

The brain 200 of FIG. 4 also indicates neural activity in a second region 211 in a second hemisphere 204 of the brain. In general, each hemisphere 202, 204 of the brain 200 is responsible for exerting primary or majority control over motor and/or sensory functions on the opposing or "contralateral" side of the patient's body. For example, the neural activity in the first region 210 shown in FIG. 4 may be generally associated with the movement of fingers on a patient's right hand, whereas the second region 211 in the right hemisphere 204 may be generally associated with movement of fingers on the patient's left hand. This second region 211, like the first region 210, may have a high-intensity area 213 and a low-intensity area 215 in which different levels of neural activity related to movement of the patient's left-hand fingers occur. The first region 210 may be associated with a body part or parts (in this example, the fingers of the right hand) and the second region 211 may be associated with a contralateral homotypic body part (in this case the fingers of the left hand), i.e., another body part having the same or an analogous structure or function as, but contralateral to, the first body part. This is one example of a body function (movement of the left fingers) that may be a corollary to another body function (movement of the right fingers).

The neural activity in the first region 210, however, can be impaired. In one embodiment, the diagnostic procedure 102 begins by taking an image of the brain 200 that is capable of detecting neural activity to determine whether the intended neural activity associated with the particular neural function of interest is occurring at the region of the brain 200 where it normally occurs according to the functional organization of the brain. FIG. 5 is an exemplary image of the brain 200 after the first region 210 has been affected (e.g., from a stroke, trauma or other cause). As shown in FIG. 5, the neural activity that controlled the neural-function for moving the fingers of the right hand no longer occurs in the first region 210. The first region 210 is thus "inactive," which is expected to result in a corresponding loss of the movement and/or sensation in the fingers. In some instances, the damage to the brain 200 may result in only a partial loss of the neural activity in the damaged region. In either case, the image shown in FIG. 5 establishes that the loss of the neural-function is related to the diminished neural activity in the first region 210. The brain 200 may accordingly recruit other neurons to perform neural activity for the affected neural-function (i.e., neuroplasticity), or the neural activity may not be present at any location in the brain. As suggested in FIG. 5, a corollary neural function associated with the contralateral homotypic body part (in this case, movement of the fingers of the left hand), which is associated with the second region 211, may remain largely unimpaired. It is worth noting that the second region 211 associated with the corollary body function is at a contralateral homotopic location to the first region 210, i.e., the location of the second region 211 on the second hemisphere 204 is homologous or generally corresponds to the location of the second region 210 on the first hemisphere 202.

FIG. 6 is an image of the brain 200 illustrating a plurality of potential stimulation sites 220 and 230 for effectuating the neural-function that was originally performed in the first region 210 shown in FIG. 4. FIGS. 5 and 6 show an example of neuroplasticity in which the brain compensates for a loss of neural-function in one region of the brain by recruiting other regions of the brain to perform neural activity for carrying out the affected neural-function. It is worth noting that a first potential stimulation site 220 is in the same hemisphere 202 as the first region 210 shown in FIG. 4. Since this first stimulation site 220 is on the same side of the body as the first region 210, it may be referred to as being "ipsilateral" to the first region 210. As the first region 210 in the left hemisphere 202 of the brain controls movement on the right side of the body, this first potential stimulation site 220 also may be said to be contralateral to the body function impaired by the inactive status of the first region 210. The second potential stimulation site 230, in contrast, is in the right hemisphere 204 of the brain 200 and is therefore contralateral to the first region 210 and ipsilateral to the impaired body function associated with the first region 210.

The two hemispheres 202 and 204 of the brain 200 are connected via the corpus callosum, which facilitates information transfer between the hemispheres 202 and 204. Although each hemisphere 202 or 204 generally exerts majority control over motor and/or sensory functions on the opposite or contralateral side of the patient's body, each hemisphere typically also exerts some level of control and/or influence over motor and/or sensory functions on the same or ipsilateral side of the patient's body. Moreover, through transcallosal connections, neural activity in one hemisphere may influence neural activity, e.g., neuroplasticity, in the opposite hemisphere. The location in the brain 200 that exerts influence on an ipsilateral body function frequently is proximate to or subsumed within the location of the brain associated with a corollary body function. Hence, as suggested in FIG. 6, the second potential stimulation site 230, which is ipsilateral to the body function associated with the inactive first region 210, may lie within the second region 211 of the brain. As discussed above in connection with FIG. 4, this second region 211 may be associated with a corollary to the impaired body function. In the particular example mentioned above wherein the first region 210 (which resides within the left hemisphere 202) is associated with movement of the fingers of the patient's right hand, the second potential stimulation site 230 may be positioned proximate to or within a region of the brain (i.e., the second region 211, which resides within the right hemisphere 204) associated with movement of the contralateral homotypic body part, namely the fingers of the patient's left hand.

The diagnostic procedure 102 may utilize the neuroplasticity that occurs in the brain to identify the location of a stimulation site that is expected to be more responsive to the results of an electrical, magnetic, sonic, genetic, biologic, and/or pharmaceutical procedure to effectuate the desired neural-function. One embodiment of the diagnostic procedure 102 involves generating the intended neural activity remotely from the first region 210 of the brain, and then detecting or sensing the location in the brain where the intended neural activity has been generated. The intended neural activity can be generated by applying an input that causes a signal to be sent to the brain. For example, in the case of a patient having an impaired limb, the affected limb is moved and/or stimulated while the brain is scanned using a known imaging technique that can detect neural activity (e.g., functional MRI, positron emission tomography, etc.). In one specific embodiment, the affected limb can be moved by a practitioner or the patient, stimulated by sensory tests (e.g., pricking), or subject to peripheral electrical stimulation. The movement/stimulation of the affected limb produces a peripheral neural signal from the limb that is expected to generate a response neural activity in the brain. The location in the brain where this response neural activity is present can be identified using the imaging technique. FIG. 6, for example, can be created by moving the affected fingers and then noting where neural activity occurs in response to the peripheral stimulus. By peripherally generating the intended neural activity, this embodiment may accurately identify where the brain has recruited matter (i.e., sites 220 and 230) to perform the intended neural activity associated with the neural-function.

Several particular embodiments for peripherally generating the intended neural activity are expected to be useful for therapies that involve patients who have lost volitional control of a body part. Volitional movement of a body part involves several parts of the cortex. For example, the prefrontal cortex is where the decision to move the body part occurs, the pre-motor cortex then generates the particular instructions for performing the movement, and the motor cortex then uses these instructions to send the appropriate electrical pulses to the body part via the spinal cord. The loss of volitional movement of a body part is usually caused by damage to the motor cortex. Some of the following embodiments for generating the intended neural activity may locate the site on the cortex where the brain is recruiting neurons related to the functionality of the impaired body part even though the patient is incapable of moving it.

Figure 7:
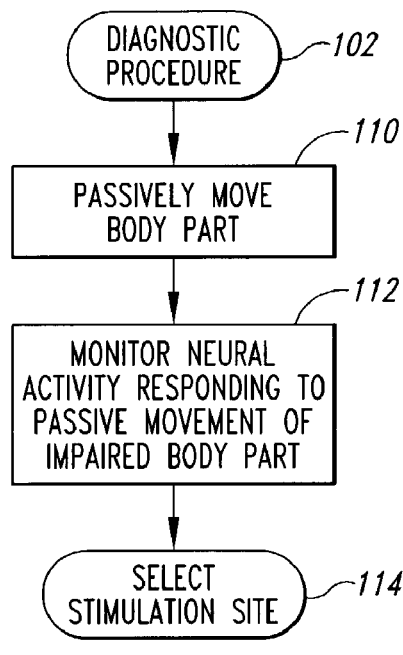
FIGS. 7–10 are flow charts illustrating various embodiments of diagnostic procedures used in embodiments of methods in accordance with the invention.

FIG. 7 is a flow chart of one embodiment of the diagnostic procedure 102 (FIG. 3) in which the intended neural activity is generated peripherally. This embodiment includes a generating phase 110 involving passively moving the impaired body part. A clinician, for example, can move the impaired body part or massage the muscles associated with the impaired body part. In an alternate embodiment, a mechanical device moves the impaired body part, such as physical therapy equipment that continually and/or intermittently moves limbs, digits and other body parts. The diagnostic procedure 102 also includes a monitoring phase 112 involving detecting the location in the cortex where passive movement of the impaired limb generates neural activity. The monitoring phase 112 is typically performed before, during, and after the generating phase 110. In one particular embodiment, the monitoring phase 112 involves: (a) imaging the neural activity in the brain using functional MRI before passively moving the impaired body part to provide a baseline indication of brain activity; (b) passively moving the impaired body part in the generating phase 110 while imaging the brain; and (c) determining the site where neural activity occurs in response to the passive movement of the impaired body part.

The passive movement of the impaired body part is expected to provide a good indication of the location in the cortex where the brain is performing neural activity that controls the impaired body part. Passively moving the impaired body part produces neural signals that travel through the spinal cord to the cortex. The neural signals then produce neural activity at a site in the brain that is associated with the function of the impaired body part. In one embodiment, this neural activity defines the "intended neural activity." The site of the intended neural activity generated by the passive movement of the impaired body part correlates well with active movement of the impaired body part. Thus, by passively moving an impaired body part and monitoring the intended neural activity that occurs in response to the passive motion, the location of the intended neural activity allows one to select, in selection phase 114, the stimulation site for applying an electrical therapy or another type of therapy.

As suggested in FIG. 6, neural activity may occur in more than one region of the brain in response to actively or passively moving the impaired body part. In general, the location at which this neural activity occurs may involve neural matter that is healthier than the neural matter associated with a lost or impaired neural function, e.g., the inactive region 210. Stimulation at such a healthier location may enhance the rate and/or extent of functional restoration of the desired neural-function. Moreover, healthier neural matter may be more sensitive or responsive to lower intensity stimulation than is damaged, impaired, or less healthy neural matter. Thus, stimulation of such healthier tissue may provide therapeutic benefit at a lower current level than stimulation applied to or proximate damaged or impaired neural matter, such as inactive region 210. As will become more evident below, the ability to employ a lower current level to achieve the same therapeutic benefit may conserve power or extend the battery life of a stimulation apparatus.

In the particular example of FIG. 6, a first potential stimulation site 220 is contralateral to the impaired body part and is in the same hemisphere 202 of the brain as the damaged first region (210 in FIG. 4) of the brain 200. A second potential stimulation site 230 is located in the other hemisphere 204 and is ipsilateral to the impaired body part that is being passively moved. In many circumstances, the second hemisphere 204 of the brain will be largely unaffected by the underlying cause of damage to the first region 210. For example, a stroke leading to inactivity in the first region 210 may cause little or no damage in the second hemisphere 204.

In circumstances where neural activity occurs at multiple locations in response to moving the impaired body part, the selection phase 114 may further include selecting one or more of the areas of the brain exhibiting such neural activity as a stimulation site. In one particular embodiment, the selection phase 114 includes selecting a stimulation site from a plurality of potential stimulation sites exhibiting such neural activity that is contralateral to a damaged location of the brain and ipsilateral to an impaired body function. Hence, in the specific example of FIG. 6, the selection phase 114 may comprise selecting the second potential stimulation site 230 as the intended stimulation site. The first potential stimulation site 220 is positioned closer to the damaged first region 210 and may not be quite as healthy as the second potential stimulation site 230, which is in the undamaged hemisphere 204 contralateral to the damaged hemisphere. As such healthier tissue may be more responsive to neural stimulation, it is anticipated that selecting an intended stimulation site at a location that is contralateral to the damaged brain tissue may provide enhance therapeutic benefits or may provide therapeutic benefit at a lower current level.

Figure 8:
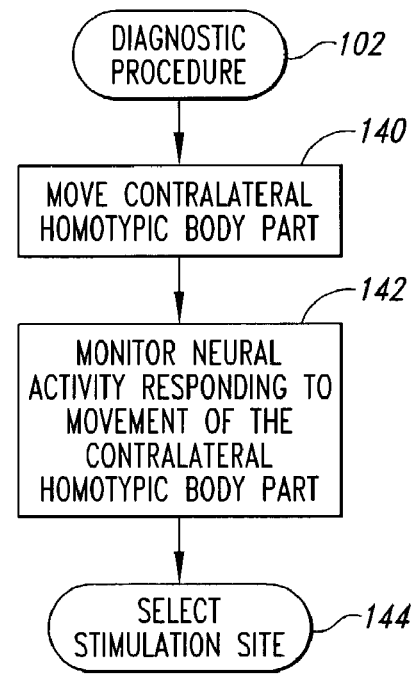

FIG. 8 is a flow chart of another embodiment of the diagnostic procedure 102. In this embodiment, the diagnostic procedure 102 includes a generating phase 140 that involves exercising a body function that is a corollary to an impaired body function. In the context of a procedure wherein the impaired body function is impaired movement of a body part, this generating phase 140 may include identifying a corresponding movement of a contralateral homotypic body part and moving that homotypic body part. Using the same example discussed above, if the patient is suffering from impaired function of the fingers of his or her right hand, the fingers of the left hand may be considered an appropriate contralateral homotypic body part and the generating phase 140 may include movement of the fingers of the left hand.

Movement of the contralateral homotypic body part can be accomplished in a variety of ways. In some of the embodiments discussed above, the patient may have little or no volitional control over movement of an impaired body part, necessitating intervention by an operator or a device to move the impaired body part. Because the contralateral homotypic body part often will have largely unimpaired function, movement of the homotypic body part in the generating phase 140 may be volitional movement of the body part by the patient. For example, the patient may be requested to flex or otherwise move the fingers of the left hand. In another embodiment, the contralateral homotypic body part may be moved passively as discussed above in connection with FIG. 7, such as by having a clinician move the homotypic body part, stimulating the muscles associated with the homotypic body part, or by employing a mechanical device.

The diagnostic procedure 102 of FIG. 8 also includes a monitoring phase 142. This monitoring phase 142 includes detecting neural activity that occurs in response to movement of the contralateral homotypic body part in the generating phase 140. This may be accomplished by monitoring neural activity in the brain while performing the generating phase in a manner analogous to the monitoring phase 112 discussed above. Using the information gathered in the monitoring phase 142, a suitable stimulation site may be selected in the selection phase 144 of FIG. 8. If neural activity is detected at multiple locations in the brain during the monitoring phase 142, the selection phase 144 may include selecting one of those locations as a stimulation site. In some circumstances, movement of the contralateral homotypic body part may generate neural activity in both hemispheres 202 and 204 of the brain. In such a circumstance, the selection phase 144 in some embodiments comprises selecting as a stimulation site a location on the brain that is ipsilateral to the impaired body function and contralateral to a damaged portion of the brain, e.g., the first region 210 shown in FIGS. 4 and 5.

In another embodiment, a generating phase (not shown) may instead comprise volitional exercise of the actual impaired body function. For example, to enhance the ability to learn a particular task (e.g., playing a musical instrument or memorizing information), the neural activity may be monitored (in a manner analogous to the monitoring phase 142 of FIG. 8) while the patient performs the task or thinks about performing the task. The potential stimulation sites can be identified in the selection phase as those areas of the brain where the neural activity has the highest intensity or the greatest increases, or those areas of the brain that other parameters indicate are being used to perform the particular task. As in the prior embodiments, the selection phase may comprise selecting a stimulation site at a location of the brain that is ipsilateral to the impaired body function (if the impaired body function is associated with one side of the body or the other) and/or contralateral to a damaged location of the brain. For example, if the deficit or impaired function is associated with a damaged area in one hemisphere of the brain, the stimulation site may be selected as a contralateral homotopic location on the opposite hemisphere of the brain.

Figure 9:
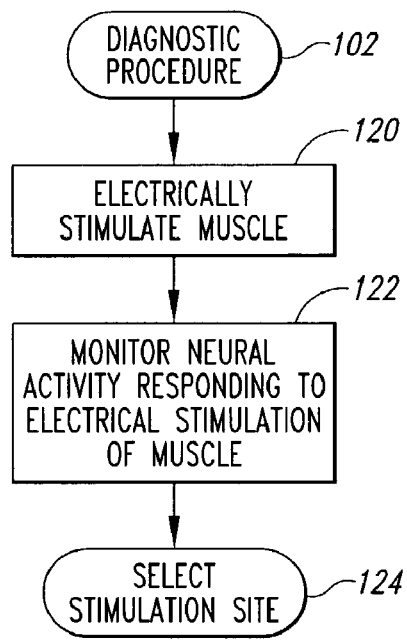

FIG. 9 is a flow chart of another embodiment of the diagnostic procedure 102. In this embodiment, the diagnostic procedure 102 includes a generating phase 120 involving electrically stimulating the muscles of the impaired body part or of a contralateral homotypic body part. The electrical stimulation can be performed using transcutaneous or subcutaneous electrodes or electrical stimulation devices. A transcutaneous device, for example, can include electrode patches that are applied to the skin and coupled to a current source. Suitable subcutaneous devices can include depth electrodes or percutaneous therapy electrodes. Such electrodes can be flexible, wire-type electrodes or rigid, needle-type electrodes. The embodiment of the diagnostic procedure 102 also includes a monitoring phase 122 in which the neural activity in the brain is monitored while performing the generating phase 120. The monitoring phase 122 can be similar to the monitoring phase 112 described above. Thus, the monitoring phase 122 determines the site where cortical neural activity occurs in response to the electrical stimulation of the muscles.

The embodiment of the diagnostic procedure 102 shown in FIG. 9 that electrically stimulates the muscles may provide enhanced-accuracy results. One reason for this is that the electrical current can be applied to only certain muscles without having to involve other muscles. As a result, it is expected that there will be less "noise" in the image of the neural activity. Such a reduction in noise may produce a more accurate indication of where the neural response is occurring in the brain, facilitating selection of a suitable stimulation site in a selection phase 124. As discussed above, in some applications the intended neural activity may occur at more than one location in the brain, identifying multiple potential stimulation sites, e.g., potential stimulation sites 220 and 230 in FIG. 6. In some embodiments, the selection phase 124 may, therefore, comprise selecting a stimulation site from a plurality of potential stimulation sites where the intended neural activity occurs. This selection may comprise selecting a stimulation site that is ipsilateral to the impaired body part and contralateral to a damaged first location (210 in FIG. 4) of the brain 200 that is or was associated with the impaired body function.

In certain applications of the embodiment shown in FIG. 9, the muscles of the impaired body part are electrically stimulated. This can help give a more direct indication of where the intended neural activity is occurring in the brain. In other applications of this embodiment, the stimulated muscles are in a homotypic body part that is contralateral to the impaired body part. In the embodiment discussed above in connection with FIG. 8, the neural-function associated with the corollary of an impaired body function was determined by moving a body part that is a contralateral homotypic body part to the impaired body part in the generating phase 140.

Figure 10:
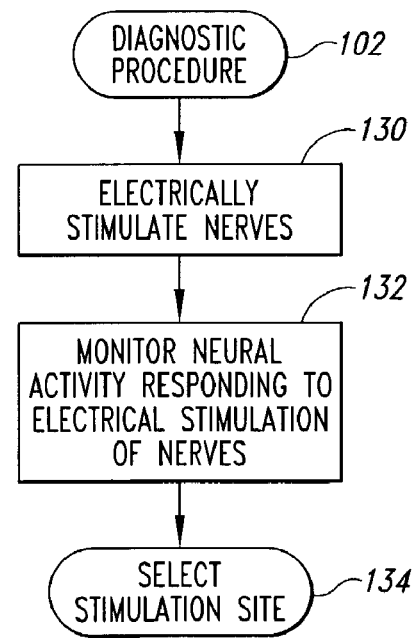

FIG. 10 is a flow diagram of yet another embodiment of the diagnostic procedure 102. In this embodiment, the diagnostic procedure 102 includes a generating phase 130 involving electrically stimulating at least one of the nerves of the impaired body part or a contralateral homotypic body part. The electrical stimulation of the nerve can be performed using a set of electrodes that are positioned proximate to the particular nerve(s) in the selected body part, and then the electrical current is applied to the electrodes. In one application of the embodiment illustrated in FIG. 10, the electrodes are positioned proximate to the particular nerves in the impaired body part. Stimulating the nerves in the impaired body part may give a relatively direct indication of the pertinent locations of the brain in the monitoring phase 132, discussed below. In another application, the electrodes may be positioned proximate to contralateral homotypic nerves in an unimpaired contralateral homotypic body part.

The diagnostic procedure 102 in FIG. 10 can also include a monitoring phase 132, which can be similar to the monitoring phase 112 described above. Thus, the monitoring phase 132 determines the site where cortical neural activity occurs in response to the electrical stimulation of the nerves. This determination can then be used in selecting a suitable stimulation site in a selection phase 134. As discussed above in connection with the embodiments of FIGS. 7–9, the selection phase 134 may comprise selecting a stimulation site from a plurality of potential stimulation sites. In some embodiments, this selection phase 134 may comprise selecting a stimulation site within the hemisphere of the brain that is ipsilateral to the damaged body part and contralateral to a damaged region of the brain (e.g., the first region 210 in FIG. 6) that is or was associated with the impaired body part.

The embodiment of the diagnostic procedure 102 shown in FIG. 10 is also expected to be useful for providing an accurate image of the intended neural activity in the cortex. Stimulating nerves may reduce the "noise" of neural activity in the brain correlated with an impaired body part. Additionally, stimulating the nerves in the impaired body part may provide an even more precise image of the response neural activity in the brain because it directly involves the nervous system without having to involve other features of the impaired body part.

Another benefit of several embodiments of the diagnostic procedures described above with reference to FIGS. 9 and 10 is that they may generate the intended neural activity in highly impaired body parts. One aspect of severely impaired body parts is that passive motion of such body parts may not generate neural activity in the brain. The electrical stimulation of the muscles and/or the nerves of the impaired body part, however, may provide more stimulus than merely passively moving the muscles. The electrical stimulus may thus generate neural activity related to the impaired body part when passive movement of the impaired body part does not produce a sufficiently adequate image.

Figure 11:
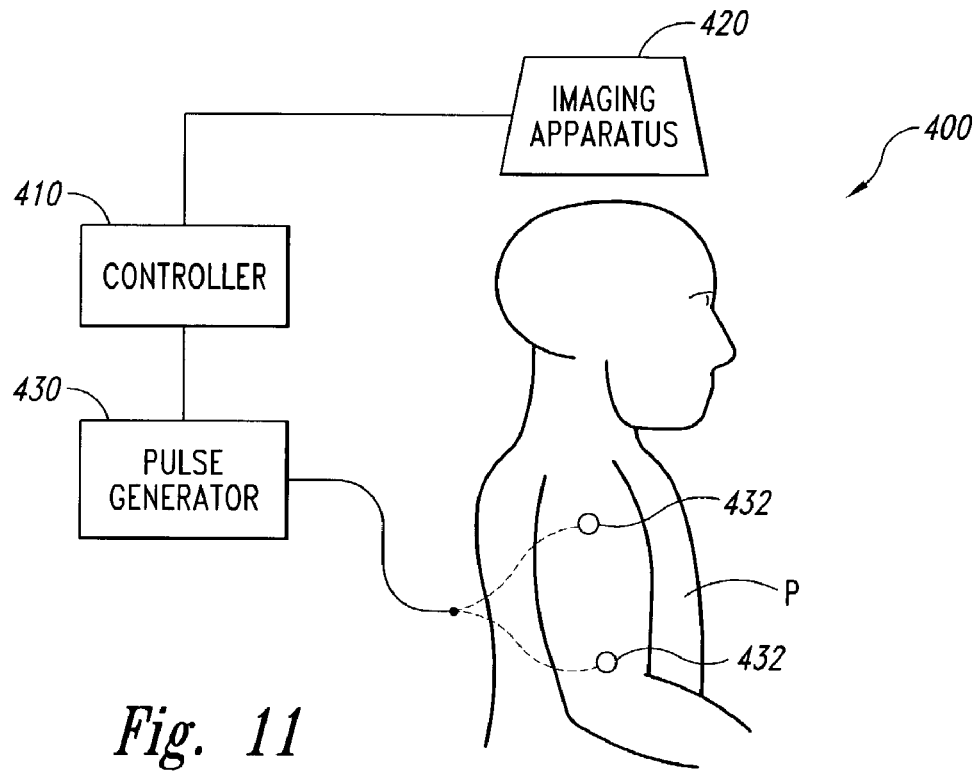
FIG. 11 is a schematic illustration of a system for carrying out the diagnostic and stimulation procedures of FIGS. 4C and 4D.

FIG. 11 schematically illustrates a system 400 for performing particular diagnostic procedures described above. The system 400 includes a controller 410, an imaging apparatus 420 coupled to the controller 410, and possibly a pulse generator 430 coupled to the controller 410. The system 400 can also include a plurality of stimulus elements 432 for providing a stimulus to the affected body part of the patient P. The procedure described with respect to FIG. 9 uses the stimulus elements 432 to stimulate the muscle of the affected body part, whereas the procedure described with respect to FIG. 10 uses the stimulus elements 432 to stimulate the nerves of the affected body part. The stimulus elements 432 can be transcutaneous or subcutaneous electrodes or electrode devices. The stimulus elements 432 can alternatively be magnetic stimulation elements that provide magnetic stimuli to the affected body part of the patient P. In the example shown in FIG. 11, the upper arm is the affected body part of the patient P. In operation, the controller 410 instructs the pulse generator 430 to provide a stimulus to the affected body part via the stimulus elements 432. As the stimulus is applied to the affected body part, the imaging apparatus 420 monitors the neural activity in the patient P and generates data corresponding to the observed neural activity.

Figure 12:
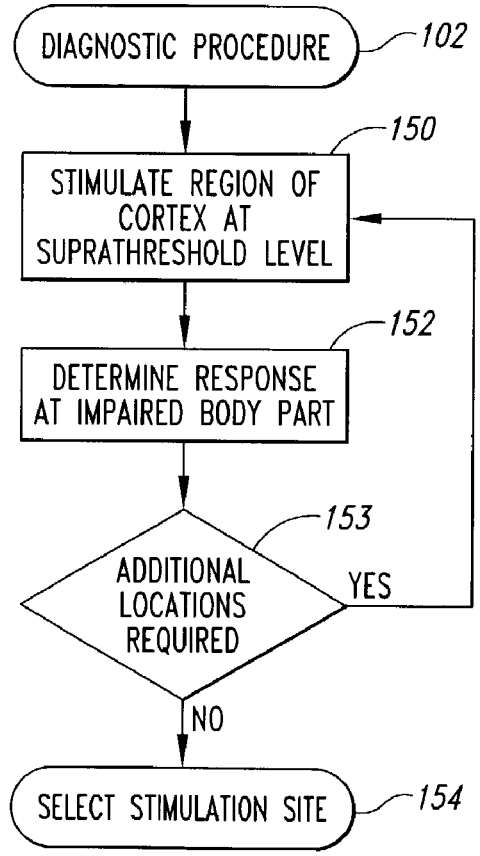
FIG. 12 is a flow chart illustrating another embodiment of a method in accordance with the invention.

FIG. 12 is a flow chart of still another embodiment of the diagnostic procedure 102 in accordance with the invention. In this embodiment, the diagnostic procedure 102 includes a generating phase 150 involving stimulating an area on the cortex at a supra-threshold level, and a monitoring phase 152 involving determining whether the supra-threshold stimulation produced a response in the impaired body part. In one embodiment, the generating phase 150 involves stimulating one or more cortical regions using a Transcranial Magnetic Stimulation (TMS) device. In another embodiment, the generating phase 150 can include implanting an electrode array having a plurality of electrodes to which an electrical current can be applied independently. The region of the cortex for implanting the electrode array can be based upon an estimate of the area where the brain is likely to perform the neural activity to control the impaired body part. After implanting the electrode array, different configurations of electrodes can be activated to apply electrical stimulation to different areas of the cortex. The generating phase 150 also typically includes applying stimulation at a supra-threshold level that will cause a motor response, an electrical response, or another type of response that can be measured at the impaired body part.

The monitoring phase 152 of this embodiment of the diagnostic procedure 102 involves measuring the response to the electrical stimulation that was applied to the cortex in the generating phase 150. The response can be detected using electrical sensors at the impaired body part or by detecting movement of the impaired body part. If no response is detected, then the particular area of the cortex to which the stimulation was applied is not likely the motor control area of the cortex associated with performing neural activity for the impaired body part. The diagnostic procedure 102 can accordingly further include a decision phase 153 in which the practitioner or a computer decides to apply stimulation to another area of the cortex by moving a TMS device to another location, or selecting another electrode configuration on the electrode array. If a response is detected at the impaired body part, then the area of the cortex to which the stimulation was applied is likely involved in performing the neural function for the impaired body part. The diagnostic procedure 102 in this embodiment can also decide to test alternate cortical stimulation regions or locations at the decision phase 153 even when a response to the stimulation is detected to further refine the area of the cortex that is performing the neural activity of the impaired body part. After testing one or, more typically, several different cortical stimulation locations, the diagnostic procedure 102 can proceed to the selection phase 154 in which the area of the cortex that provided a desired response in the impaired body part is selected as the site to apply therapeutic electrical stimulation. If the generating phase 150 generates neural activity at multiple locations of the brain, the selection phase 154 may comprise selecting a stimulation site from these multiple potential stimulation sites. In one particular embodiment, the selection phase 154 comprises selecting a stimulation site that is ipsilateral to an impaired body part and contralateral to a damaged location of the brain 200 that was formerly associated with the impaired body part.

An alternative embodiment of the diagnostic procedure 102 involves identifying a stimulation site at a second location of the brain where the neural activity has changed in response to a change in the neural-function of the patient.

This embodiment of the method does not necessarily require that the intended neural activity be generated by peripherally actuating or stimulating a body part. For example, the brain can be scanned for neural activity associated with the impaired neural-function as a patient regains use of an affected limb or learns a task over a period of time. This embodiment, however, can also include peripherally generating the intended neural activity remotely from the brain explained above.

In still another embodiment, the diagnostic procedure 102 involves identifying a stimulation site at a location of the brain where the intended neural activity is developing to perform the neural-function. This embodiment is similar to the other embodiments of the diagnostic procedure 102, but it can be used to identify a stimulation site at (a) the normal region of the brain where the intended neural activity is expected to occur according to the functional organization of the brain and/or (b) a different region where the neural activity occurs because the brain is recruiting additional matter to perform the neural-function. This particular embodiment of the method involves monitoring neural activity at one or more locations where the neural activity occurs in response to the particular neural-function of interest. For example, to enhance the ability to learn a particular task (e.g., playing a musical instrument, memorizing, etc.), the neural activity can be monitored while a person performs the task or thinks about performing the task. The stimulation sites can be defined by the areas of the brain where the neural activity has the highest intensity, the greatest increases, and/or other parameters that indicate areas of the brain that are being used to perform the particular task.

Figure 13:
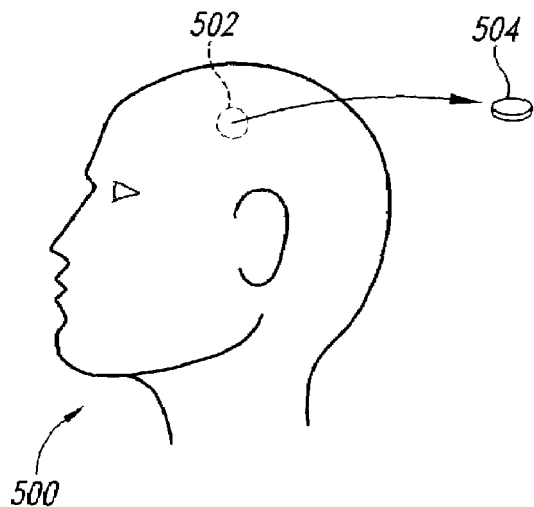
FIGS. 13 and 14 are schematic illustrations of an implanting procedure at a stage of a method in accordance with an embodiment of the invention.
Figure 14:
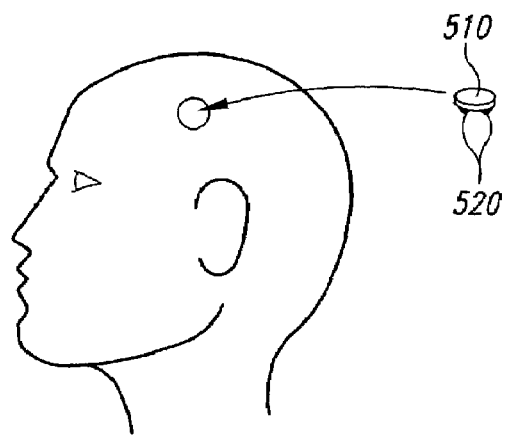

FIGS. 13 and 14 are schematic illustrations of the implanting procedure 104 described above with reference to FIG. 3 for positioning the first and second electrodes relative to a portion of the brain of a patient 500. Referring to FIG. 13, a stimulation site 502 is identified in accordance with an embodiment of the diagnostic procedure 102. In one embodiment, a skull section 504 is removed from the patient 500 adjacent to the stimulation site 502. The skull section 504 can be removed by boring a hole in the skull in a manner known in the art, or a much smaller hole can be formed in the skull using drilling techniques that are also known in the art. In general, the hole can be 0.2–4.0 cm in diameter. Referring to FIG. 14, an implantable stimulation apparatus 510 having first and second electrodes 520 can be implanted in the patient 500. Suitable techniques associated with the implantation procedure are known to practitioners skilled in the art. After the stimulation apparatus 510 has been implanted in the patient 500, a pulse system generates electrical pulses that are transmitted to the stimulation site 502 by the first and second electrodes 520. Stimulation apparatus suitable for carrying out the foregoing embodiments of methods in accordance with the invention are described in more detail below with reference to the FIGS. 16–21.

Several embodiments of methods for enhancing neural activity in accordance with the invention are expected to provide lasting results that promote the desired neural-function. Before the present invention, electrical and magnetic stimulation techniques typically stimulated the normal locations of the brain where neural activity related to the neural-functions occurred according to the functional organization of the brain. Such conventional techniques, however, may not be effective because the neurons in the "normal locations" of the brain may not be capable of carrying out the neural activity because of brain damage, disease, disorder, and/or because of variations of the location specific to individual patients. Several embodiments of methods for enhancing neural activity in accordance with the invention overcome this drawback by identifying a stimulation site based on neuroplastic activity that appears to be related to the neural-function. By first identifying a location in the brain that is being recruited to perform the neural activity, it is expected that therapies (e.g., electrical, magnetic, genetic, biologic, and/or pharmaceutical) applied to this location will be more effective than conventional techniques. This is because the location that the brain is recruiting for the neural activity may not be the "normal location" where the neuro activity would normally occur according to the functional organization of the brain. Therefore, several embodiments of methods for enhancing neural activity in accordance with the invention are expected to provide lasting results because the therapies are applied to the portion of the brain where neural activity for carrying out the neural-function actually occurs in the particular patient.

2. Electrically Inducing Desired Neural Activity

The method 100 for effectuating a neural-function can also be used to induce neural activity in a region of the brain where such neural activity is not present. As opposed to the embodiments of the method 100 described above for enhancing existing neural activity, the embodiments of the method 100 for inducing neural activity initiate the neural activity at a stimulation site where it is estimated that neuroplasticity will occur. In this particular situation, an image of the brain seeking to locate where neuroplasticity is occurring may be similar to FIG. 5. An aspect of inducing neural activity, therefore, is to develop a procedure to determine where neuroplasticity is likely to occur.

A stimulation site may be identified by estimating where the brain will likely recruit neurons for performing the neural-function. In one embodiment, the location of the stimulation site is estimated by defining a region of the brain that is proximate to the normal location where neural activity related to the neural-function is generally present according to the functional organization of the brain. An alternative embodiment for locating the stimulation site includes determining where neuroplasticity has typically occurred in patients with similar symptoms. For example, if the brain typically recruits a second region of the cortex to compensate for a loss of neural activity in the normal region of the cortex, then the second region of the cortex can be selected as the stimulation site either with or without imaging the neural activity in the brain.

Several embodiments of methods for inducing neural activity in accordance with the invention are also expected to provide lasting results that initiate and promote a desired neural-function. By first estimating the location of a stimulation site where desired neuroplasticity is expected to occur, therapies applied to this location may be more effective than conventional therapies for reasons that are similar to those explained above regarding enhancing neural activity. Additionally, methods for inducing neural activity may be easier and less expensive to implement because they do not require generating neural activity and/or imaging the brain to determine where the intended neural activity is occurring before applying the therapy.

3. Applications of Methods for Electrically Stimulating Regions of the Brain

The foregoing methods for enhancing existing neural activity or inducing new neural activity are expected to be useful for many applications. As explained above, several embodiments of the method 100 involve determining an efficacious location of the brain to enhance or induce an intended neural activity that causes the desired neural-functions to occur. Additional therapies can also be implemented in combination with the electrical stimulation methods described above. Several specific applications using embodiments of electrical stimulation methods in accordance with the invention either alone or with adjunctive therapies will now be described, but it will be appreciated that the methods in accordance with the invention can be used in many additional applications.

a. General Applications

The embodiments of the electrical stimulation methods described above are expected to be particularly useful for rehabilitating a loss of mental functions, motor functions and/or sensory functions caused by damage to the brain. In a typical application, the brain has been damaged by a stroke or trauma (e.g., automobile accident). The extent of the particular brain damage can be assessed using functional MRI or another appropriate imaging technique as explained above with respect to FIG. 5. A stimulation site can then be identified by: (a) peripherally stimulating a body part that was affected by the brain damage to induce the intended neural activity and determining the location where a response neural activity occurs; (b) determining where the neural activity has changed as a patient gains more use of the affected body part; (c) estimating the location that the brain may recruit neurons to carry out the neural activity that was previously performed by the damaged portion of the brain; and/or (d) determining a location in the brain hemisphere ipsilateral to the affected body part that is associated with a function that is a corollary to an impaired function of the affected body part. An electrical stimulation therapy can then be applied to the selected stimulation site by placing the first and second electrodes relative to the stimulation site to apply an electrical current in that portion of the brain. As explained in more detail below, it is expected that applying an electrical current to the portion of the brain that has been recruited to perform the neural activity related to the affected body part will produce a lasting neurological effect for rehabilitating the affected body part.

Several specific applications are expected to have a stimulation site in the cortex because neural activity in this part of the brain effectuates motor functions and/or sensory functions that are typically affected by a stroke or trauma. In these applications, the electrical stimulation can be applied directly to the pial surface of the brain or at least proximate to the pial surface (e.g., the dura mater, the fluid surrounding the cortex, or neurons within the cortex). Suitable devices for applying the electrical stimulation to the cortex are described in detail with reference to FIGS. 16–21.

The electrical stimulation methods can also be used with adjunctive therapies to rehabilitate damaged portions of the brain. In one embodiment, the electrical stimulation methods can be combined with behavioral therapy and/or drug therapies to rehabilitate an affected neural function. For example, if a stroke patient has lost the use of a limb, the patient can be treated by applying the electrical therapy to a stimulation site where the intended neural activity is present while the affected limb is also subject to physical therapy. An alternative embodiment can involve applying the electrical therapy to the stimulation site and chemically treating the patient using amphetamines or other suitable drugs.

The embodiments of the electrical stimulation methods described above are also expected to be useful for treating brain diseases, such as Alzheimer's, Parkinson's, and other brain diseases. In this application, the stimulation site can be identified by monitoring the neural activity using functional MRI or other suitable imaging techniques over a period of time to determine where the brain is recruiting material to perform the neural activity that is being affected by the disease. It may also be possible to identify the stimulation site by having the patient try to perform an act that the particular disease has affected, and monitoring the brain to determine whether any response neural activity is present in the brain. After identifying where the brain is recruiting additional matter, the electrical stimulation can be applied to this portion of the brain. It is expected that electrically stimulating the regions of the brain that have been recruited to perform the neural activity which was affected by the disease will assist the brain in offsetting the damage caused by the disease.

The embodiments of the electrical stimulation methods described above are also expected to be useful for treating neurological disorders, such as depression, passive-aggressive behavior, weight control, and other disorders. In these applications, the electrical stimulation can be applied to a stimulation site in the cortex or another suitable part of the brain where neural activity related to the particular disorder is present. The embodiments of electrical stimulation methods for carrying out the particular therapy can be adapted to either increase or decrease the particular neural activity in a manner that produces the desired results. For example, an amputee may feel phantom sensations associated with the amputated limb. This phenomenon can be treated by applying an electrical pulse that reduces the phantom sensations. The electrical therapy can be applied so that it will modulate the ability of the neurons in that portion of the brain to execute sensory functions.

b. Pulse Forms and Potentials

The electrical stimulation methods in accordance with the invention can use several different pulse forms to facilitate or effectuate the desired neuroplasticity.

The pulses can be a bi-phasic or monophasic stimulus that is applied to achieve a desired potential in a sufficient percentage of a population of neurons at the stimulation site. In one embodiment, the pulse form has a frequency of approximately 2–1000 Hz, but the frequency may be particularly useful in the range of approximately 40–200 Hz. For example, initial clinical trials are expected to use a frequency of approximately 50–100 Hz. The pulses can also have pulse widths of approximately 10 μs-100 ms, or more specifically the pulse width can be approximately 20–200 μs. For example, a pulse width of 50–100 μs may produce beneficial results.

It is expected that one particularly useful application of the invention involves enhancing or inducing neuroplasticity by raising the membrane potential of neurons to bring the neurons closer to the threshold level for firing an action potential. Because the stimulation raises the membrane potential of the neurons, it is expected that these neurons are more likely to "fire" an action potential in response to excitatory input at a lower level.

Figure 15:
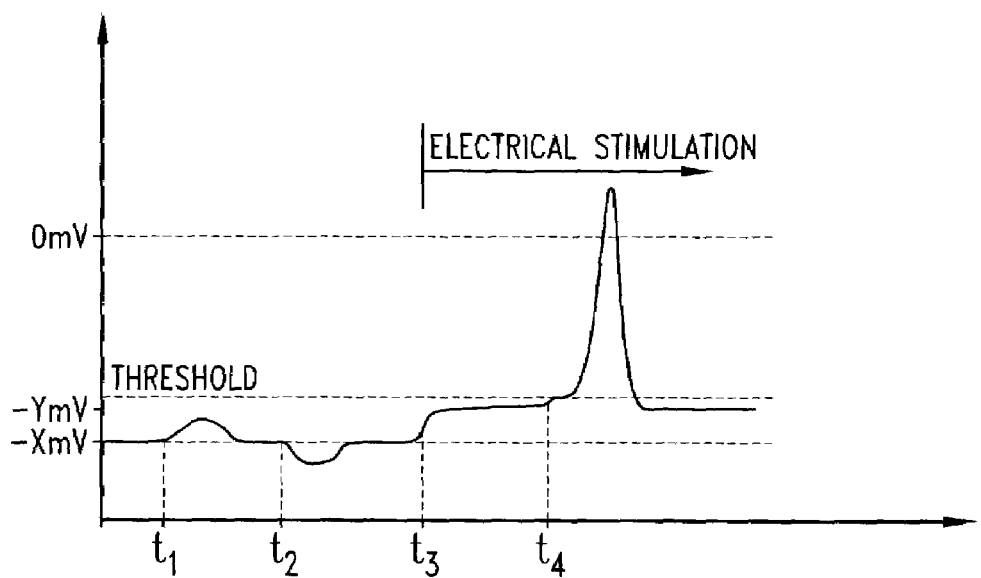
FIG. 15 is a graph illustrating firing an "action potential" associated with stimulated neural activity in accordance with one embodiment of the invention.

FIG. 15 is a graph illustrating applying a subthreshold potential to the neurons N1–N3 of FIG. 1. At times $t_1$ and $t_2$, the excitory/inhibitory inputs from other neurons do not "bridge-the-gap" from the resting potential at –X mV to the threshold potential. At time $t_3$, the electrical stimulation is applied to the brain to raise the potential of neurons in the stimulated population such that their potential is at –Y mV. As such, at time $t_4$ when the neurons receive another excitatory input, even a small input exceeds the gap between the raised potential –Y mV and the threshold potential to induce action potentials in these neurons. For example, if the resting potential is approximately –70 mV and the threshold potential is approximately –50 mV, then the electrical stimulation can be applied to raise the potential of a sufficient number of neurons to approximately −52 to −60 mV.

The actual electrical potential applied to electrodes implanted in the brain to achieve a subthreshold potential stimulation will vary according to the individual patient, the type of therapy, the type of electrodes, and other factors. In general, the pulse form of the electrical stimulation (e.g., the frequency, pulse width, wave form, and voltage potential) is selected to raise the potential in a sufficient number neurons at the stimulation site to a level that is less than a threshold potential for a statistical portion of the neurons in the population. The pulse form, for example, can be selected so that the applied voltage of the stimulus achieves a change in the potential of approximately 10%–95%, and more specifically of 60%–80%, of the difference between the unstimulated resting potential and the threshold potential.

In one specific example of a subthreshold application for treating a patient's hand, electrical stimulation is not initially applied to the stimulation site. Although physical therapy related to the patient's hand may cause some activation of a particular population of neurons that is known to be involved in "hand function," only a low level of activation might occur because physical therapy only produces a low level of action potential generation in that population of neurons. However, when the subthreshold electrical stimulation is applied, the membrane potentials of the neurons in the stimulated population are elevated. These neurons now are much closer to the threshold for action potential formation such that when the same type of physical therapy is given, this population of cells will have a higher level of activation because these cells are more likely to fire action potentials.

Subthreshold stimulation may produce better results than simply stimulating the neurons with sufficient energy levels to exceed the threshold for action potential formation. One aspect of subthreshold stimulation is to increase the probability that action potentials will occur in response to the ordinary causes of activation—such as behavioral therapy. This will allow the neurons in this functional network to become entrained together, or "learn" to become associated with these types of activities. If neurons are given so much electricity that they continually fire action potentials without additional excitatory inputs (suprathreshold stimulation), this will create "noise" and disorganization that will not likely cause improvement in function. In fact, neurons that are "overdriven" soon deplete their neurotransmitters and effectively become silent.

The application of a subthreshold stimulation is very different than suprathreshold stimulation. Subthreshold stimulation in accordance with several embodiments of the invention, for example, does not intend to directly make neurons fire action potentials with the electrical stimulation in a significant population of neurons at the stimulation site. Instead, subthreshold stimulation attempts to decrease the "activation energy" required to activate a large portion of the neurons at the stimulation site. As such, subthreshold stimulation in accordance with certain embodiments of the invention is expected to increase the probability that the neurons will fire in response to the usual intrinsic triggers, such as trying to move a limb, physical therapy, or simply thinking about movement of a limb, etc. Moreover, coincident stimulation associated with physical therapy is expected to increase the probability that the action potentials that are occurring with an increased probability due to the subthreshold stimulation will be related to meaningful triggers, and not just "noise."

The stimulus parameters set forth above, such as a frequency selection of approximately 50–100 Hz and an amplitude sufficient to achieve an increase of 60% to 80% of the difference between the potential and the threshold potential are specifically selected so that they will increase the resting membrane potential of the neurons, thereby increasing the likelihood that they will fire action potentials, without directly causing action potentials in most of the neuron population. In addition, and as explained in more detail below with respect to FIGS. 16–21, several embodiments of stimulation apparatus in accordance with the invention are designed to precisely apply a pulse form that produces subthreshold stimulation by selectively stimulating regions of the cerebral cortex of approximately 1–2 cm (the estimated size of a "functional unit" of cortex), directly contacting the pial surface with the electrodes to consistently create the same alterations in resting membrane potential, and/or biasing the electrodes against the pial surface to provide a positive connection between the electrodes and the cortex.

B. Devices for Electrically Stimulating Regions of the Brain

FIGS. 16–21 illustrate stimulation apparatus in accordance with several embodiments of the invention for electrically stimulating regions of the brain in accordance with one or more of the methods described above. The devices illustrated in FIGS. 16–21 are generally used to stimulate a region of the cortex proximate to the pial surface of the brain (e.g., the dura mater, the pia mater, the fluid between the dura mater and the pia mater, and a depth in the cortex outside of the white matter of the brain). The devices can also be adapted for stimulating other portions of the brain in other embodiments. A variety of other useful stimulation apparatus are detailed in U.S. patent application Publication Ser. No. 2002/0,087,201, the entirety of which is incorporated herein by reference. In addition, other suitable stimulation apparatus may be apparent to those skilled in the art in view of the present disclosure.

1. Implantable Stimulation Apparatus with Integrated Pulse Systems

Figure 16:
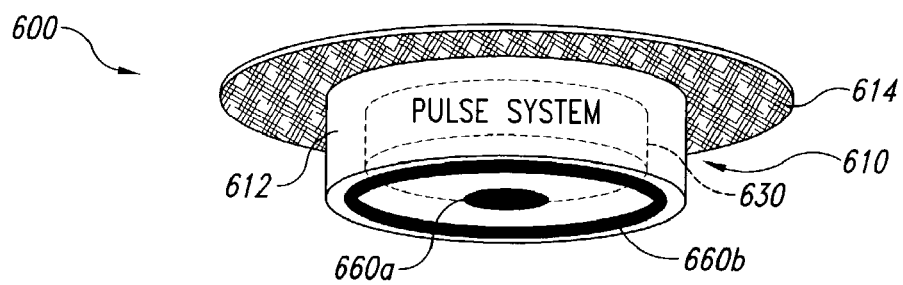
FIG. 16 is an isometric view of an implantable stimulation apparatus in accordance with one embodiment of the invention.
Figure 17:
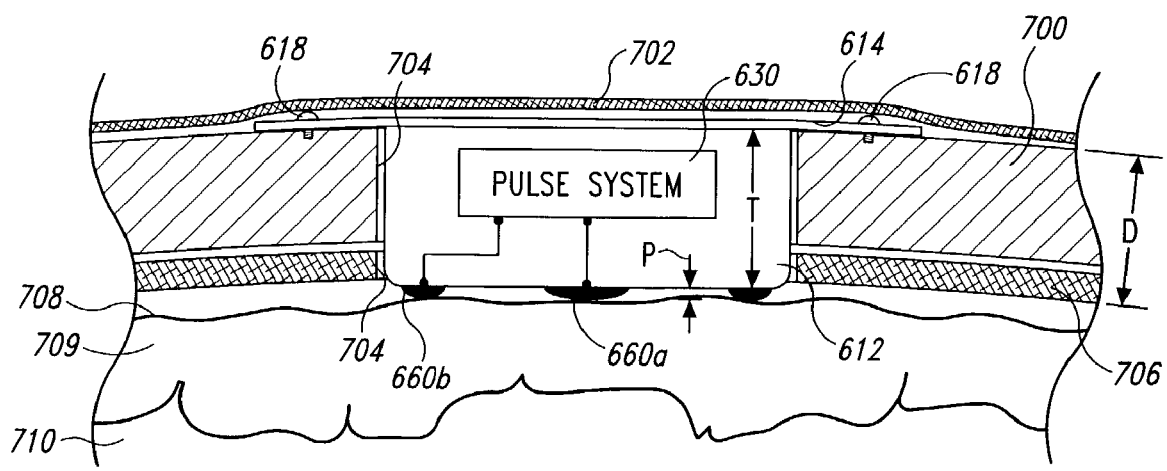
FIG. 17 is a cross-sectional view schematically illustrating a part of an implantable stimulation apparatus in accordance with an embodiment of the invention.

FIG. 16 is an isometric view and FIG. 17 is a cross-sectional view of a stimulation apparatus 600 in accordance with an embodiment of the invention for stimulating a region of the cortex proximate to the pial surface. In one embodiment, the stimulation apparatus 600 includes a support member 610, an integrated pulse-system 630 (shown schematically) carried by the support member 610, and first and second electrodes 660 (identified individually by reference numbers 660a and 660b). The first and second electrodes 660 are electrically coupled to the pulse system 630. The support member 610 can be configured to be implanted into the skull or another intracranial region of a patient. In one embodiment, for example, the support member 610 includes a housing 612 and an attachment element 614 connected to the housing 612. The housing 612 can be a molded casing formed from a biocompatible material that has an interior cavity for carrying the pulse system 630. The housing can alternatively be a biocompatible metal or another suitable material. The housing 612 can have a diameter of approximately 1–4 cm, and in many applications the housing 612 can be 1.5–2.5 cm in diameter. The housing 612 can also have other shapes (e.g., rectilinear, oval, elliptical) and other surface dimensions. The stimulation apparatus 600 can weigh 35 g or less and/or occupy a volume of 20 cc or less. The attachment element 614 can be a flexible cover, a rigid plate, a contoured cap, or another suitable element for holding the support member 610 relative to the skull or other body part of the patient. In one embodiment, the attachment element 614 is a mesh, such as a biocompatible polymeric mesh, metal mesh, or other suitable woven material. The attachment element 614 can alternatively be a flexible sheet of Mylar, a polyester, or another suitable material.

FIG. 17, more specifically, is a cross-sectional view of the stimulation apparatus 600 after it has been implanted into a patient in accordance with an embodiment of the invention. In this particular embodiment, the stimulation apparatus 600 is implanted into the patient by forming an opening in the scalp 702 and cutting a hole 704 through the skull 700 and through the dura mater 706. The hole 704 should be, sized to receive the housing 612 of the support member 610, and in most applications, the hole 704 should be smaller than the attachment element 614. A practitioner inserts the support member 610 into the hole 704 and then secures the attachment element 614 to the skull 700. The attachment element 614 can be secured to the skull using a plurality of fasteners 618 (e.g., screws, spikes, etc.) or an adhesive. In an alternative embodiment, a plurality of downwardly depending spikes can be formed integrally with the attachment element 614 to define anchors that can be driven into the skull 700.

The embodiment of the stimulation apparatus 600 shown in FIG. 17 is configured to be implanted into a patient so that the electrodes 660 contact a desired portion of the brain at the stimulation site. The housing 612 and the electrodes 660 can project from the attachment element 614 by a distance "D" such that the electrodes 660 are positioned at least proximate to the pia mater 708 surrounding the cortex 709. The electrodes 660 can project from a housing 612 as shown in FIG. 17, or the electrodes 660 can be flush with the interior surface of the housing 612. In the particular embodiment shown in FIG. 17, the housing 612 has a thickness "T" and the electrodes 660 project from the housing 612 by a distance "P" so that the electrodes 660 press against the surface of the pia mater 708. The thickness of the housing 612 can be approximately 0.5–4 cm, and is more generally about 1–2 cm. The configuration of the stimulation apparatus 600 is not limited to the embodiment shown in FIGS. 16 and 17, but rather the housing 612, the attachment element 614, and the electrodes 660 can be configured to position the electrodes in several different regions of the brain. For example, in an alternate embodiment, the housing 612 and the electrodes 660 can be configured to position the electrodes deep within the cortex 709, and/or a deep brain region 710. In general, the electrodes can be flush with the housing or extend 0.1 mm to 5 cm from the housing. More specific embodiments of pulse system and electrode configurations for the stimulation apparatus will be described below.

Several embodiments of the stimulation apparatus 600 are expected to be more effective than existing transcranial electrical stimulation devices and transcranial magnetic stimulation devices. It will be appreciated that much of the power required for transcranial therapies is dissipated in the scalp and skull before it reaches the brain. In contrast to conventional transcranial stimulation devices, the stimulation apparatus 600 is implanted so that the electrodes are at least proximate to the pial surface of the brain 708. Several embodiments of methods in accordance with the invention can use the stimulation apparatus 600 to apply an electrical therapy directly to the pia mater 708, the dura mater 706, and/or another portion of the cortex 709 at significantly lower power levels than existing transcranial therapies. For example, a potential of approximately 1 mV to 10 V can be applied to the electrodes 660; in many instances a potential of 100 mV to 5 V can be applied to the electrodes 660 for selected applications. It will also be appreciated that other potentials can be applied to the electrodes 660 of the stimulation apparatus 600 in accordance with other embodiments of the invention.

Selected embodiments of the stimulation apparatus 600 are also capable of applying stimulation to a precise stimulation site. Again, because the stimulation apparatus 600 positions the electrodes 660 at least proximate to the pial surface 708, precise levels of stimulation with good pulse shape fidelity will be accurately transmitted to the stimulation site in the brain. It will be appreciated that transcranial therapies may not be able to apply stimulation to a precise stimulation site because the magnetic and electrical properties of the scalp and skull may vary from one patient to another such that an identical stimulation by the transcranial device may produce a different level of stimulation at the neurons in each patient. Moreover, the ability to focus the stimulation to a precise area is hindered by delivering the stimulation transcranially because the scalp, skull and dura all diffuse the energy from a transcranial device. Several embodiments of the stimulation apparatus 600 overcome this drawback because the electrodes 660 are positioned under the skull 700 such that the pulses generated by the stimulation apparatus 600 are not diffused by the scalp 702 and skull 700.

2. Integrated Pulse Systems for Implantable Stimulation Apparatus

The pulse system 630 shown in FIGS. 16 and 17 generates and/or transmits electrical pulses to the electrodes 660 to create an electrical field at a stimulation site in a region of the brain. The particular embodiment of the pulse system 630 shown in FIG. 17 is an "integrated" unit in that is carried by the support member 610. The pulse system 630, for example, can be housed within the housing 612 so that the electrodes 660 can be connected directly to the pulse system 630 without having leads outside of the stimulation apparatus 600. The distance between the electrodes 660 and the pulse system 630 can be less than 4 cm, and it is generally 0.10 to 2.0 cm. The stimulation apparatus 600 can accordingly provide electrical pulses to the stimulation site without having to surgically create tunnels running through the patient to connect the electrodes 660 to a pulse generator implanted remotely from the stimulation apparatus 600. It will be appreciated, however, that alternative embodiments of stimulation apparatus in accordance with the invention can include a pulse system implanted separately from the stimulation apparatus 600 in the cranium or an external pulse system. Several particular embodiments of pulse systems that are suitable for use with the stimulation apparatus 600 will now be described in more detail.

Figure 18:
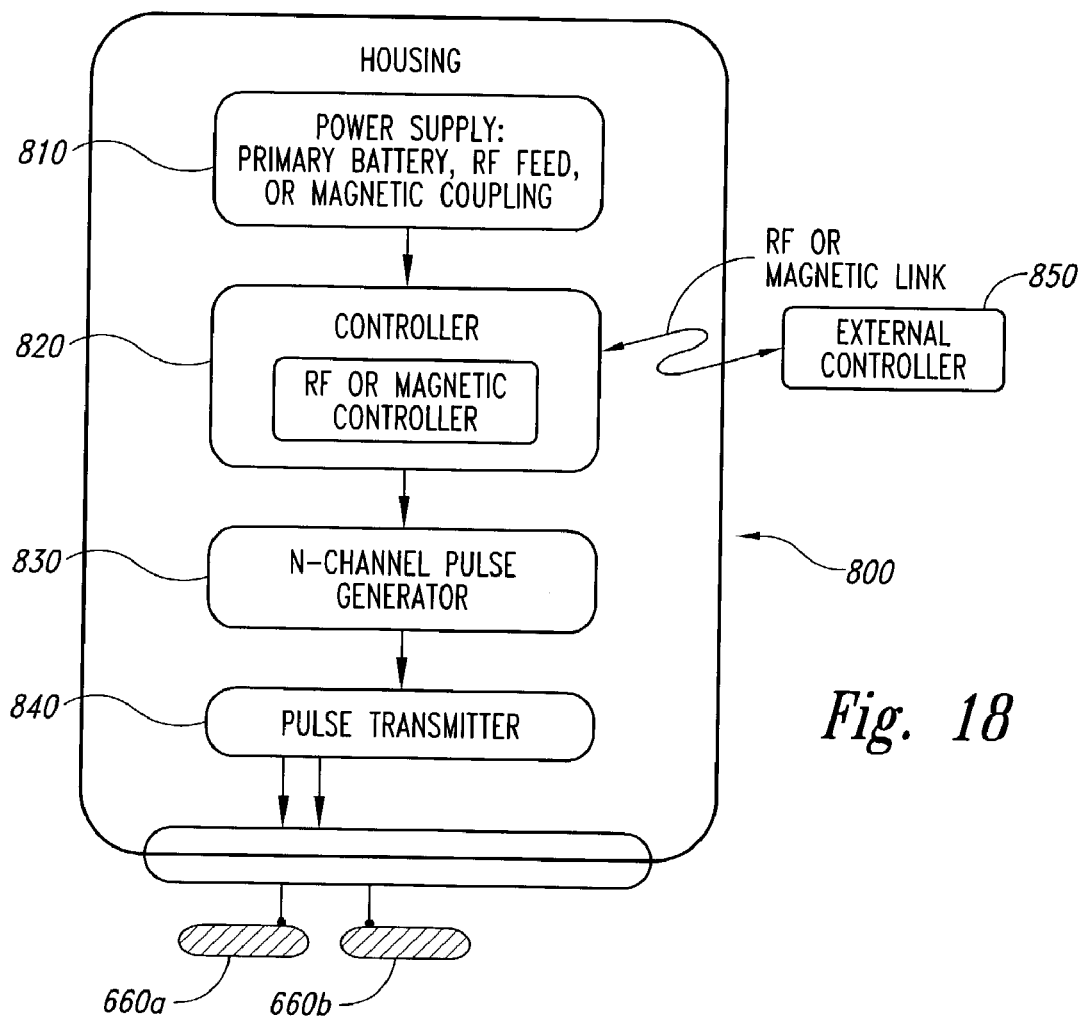
FIG. 18 is a schematic illustration of a pulse system in accordance with one embodiment of the invention.
Figure 19:
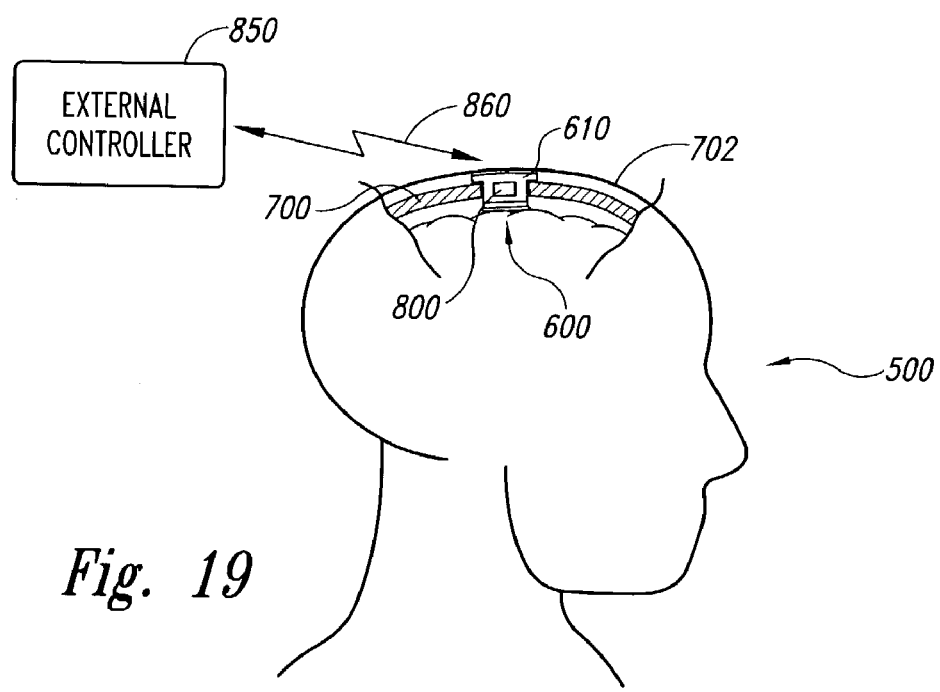
FIG. 19 is a schematic illustration of an implanted stimulation apparatus and an external controller in accordance with an embodiment of the invention.

FIGS. 18 and 19 schematically illustrate an integrated pulse system 800 in accordance with one embodiment of the invention for being implanted in the cranium within the stimulation apparatus 600. Referring to FIG. 18, the pulse system 800 can include a power supply 810, an integrated controller 820, a pulse generator 830, and a pulse transmitter 840. The power supply 810 can be a primary battery, such as a rechargeable battery or another suitable device for storing electrical energy. In alternative embodiments, the power supply 810 can be an RF transducer or a magnetic transducer that receives broadcast energy emitted from an external power source and converts the broadcast energy into power for the electrical components of the pulse system 800. The integrated controller 820 can be a wireless device that responds to command signals sent by an external controller 850. The integrated controller 820, for example, can communicate with the external controller 850 by RF or magnetic links 860. The integrated controller 820 provides control signals to the pulse generator 830 in response to the command signals sent by the external controller 850. The pulse generator 830 can have a plurality of channels that send appropriate electrical pulses to the pulse transmitter 840, which is coupled to the electrodes 660. Suitable components for the power supply 810, the integrated controller 820, the pulse generator 830, and the pulse transmitter 840 are known to persons skilled in the art of implantable medical devices.

Referring to FIG. 19, the pulse system 800 can be carried by the support member 610 of the stimulation apparatus 600 in the manner described above with reference to FIGS. 16 and 17. The external controller 850 can be located externally to the patient 500 so that the external controller 850 can be used to control the pulse system 800. In one embodiment, several patients that require a common treatment can be simultaneously treated using a single external controller 850 by positioning the patients within the operating proximity of the controller 850. In an alternative embodiment, the external controller 850 can contain a plurality of operating codes and the integrated controller 820 for a particular patient can have an individual operating code. A single controller 850 can thus be used to treat a plurality of different patients by entering the appropriate operating code into the controller 850 corresponding to the particular operating codes of the integrated controllers 820 for the patients.

2. Implantable Stimulation Apparatus with External Pulse Systems

Figure 20:
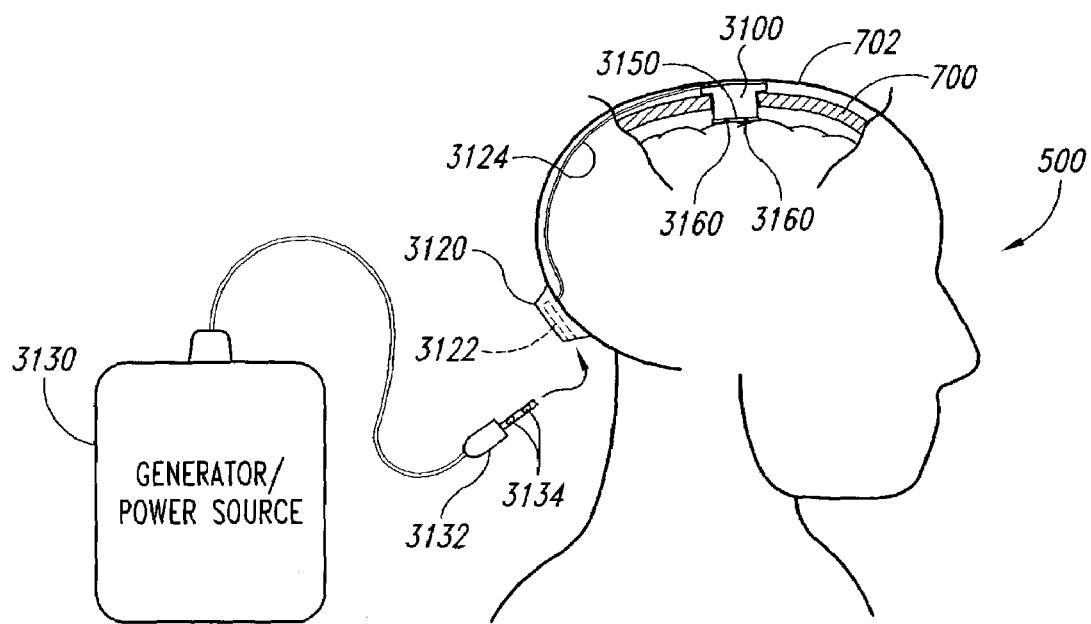
FIG. 20 is a cross-sectional view schematically illustrating a portion of an implantable stimulation apparatus having an external power source and pulse generator in accordance with an embodiment of the invention.

FIG. 20 is a schematic cross-sectional view of one embodiment of an implantable stimulation apparatus 3100 having external pulse systems. This stimulation apparatus 3100 has a biasing element 3150 to which a plurality of electrodes 3160 are attached. It will be appreciated that the stimulation apparatus 3100 may not include the biasing element 3150, but may instead have a less flexible arrangement similar to that of the stimulation apparatus 600 of FIGS. 16–19. The stimulation apparatus 3100 can also include an external receptacle 3120 having an electrical socket 3122 and an implanted lead line 3124 coupling the electrodes 3160 to contacts (not shown) in the socket 3122. The lead line 3124 can be implanted in a subcutaneous tunnel or other passageway in a manner known to a person skilled and art.

The stimulation apparatus 3100, however, does not have an internal pulse system carried by the portion of the device that is implanted in the skull 700 of the patient 500. The stimulation apparatus 3100 receives electrical pulses from an external pulse system 3130. The external pulse system 3130 can have an electrical connector 3132 with a plurality of contacts 3134 configured to engage the contacts within the receptacle 3120. The external pulse system 3130 can also have a power supply, controller, pulse generator, and pulse transmitter to generate the electrical pulses. In operation, the external pulse system 3130 sends electrical pulses to the stimulation apparatus 3100 via the connector 3132, the receptacle 3120, and the lead line 3124.

3. Alternate Embodiments of Implantable Stimulation Apparatus

Figure 21:
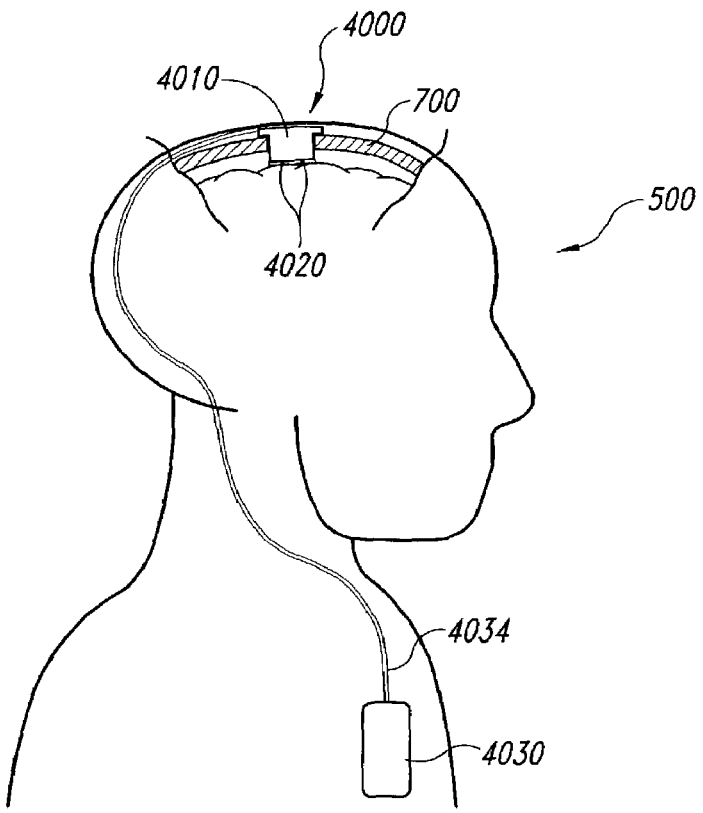
FIG. 21 is a schematic illustration of an implantable stimulation apparatus in accordance with an embodiment of the invention.

FIG. 21 is a schematic illustration of a stimulation apparatus 4000 together with an internal pulse system 4030 in accordance with another embodiment of the invention. The stimulation apparatus 4000 can include a support member 4010, a biasing element 4015 carried by the support member 4010, and a plurality of electrodes 4020 carried by the biasing element 4015. The internal pulse system 4030 can be similar to any of the integrated pulse systems described above with reference to FIGS. 16-19, but the internal pulse system 4030 is not an integrated pulse system because it is not carried by the housing 4010. The internal pulse system 4030 can be coupled to the electrodes 4020 by a cable 4034. In a typical application, the cable 4034 is implanted subcutaneously in a tunnel from a subclavicular region, along the back of the neck, and around the skull. The stimulation apparatus 4000 can also include any other suitable electrode configuration.

From the foregoing, it will be appreciated that specific embodiments of the invention have been described herein for purposes of illustration, but that various modifications may be made without deviating from the spirit and scope of the invention. Accordingly, the invention is not limited except as by the appended claims. All of the U.S. patents, U.S. patent applications, and other references noted above are incorporated herein by reference.

The invention claimed is:

1. A method of effectuating a neural-function of a patient that has an impaired body part affected by damage to a first location of a first hemisphere of a brain of the patient, comprising:

selecting a stimulation site by (a) generating an intended neural activity by triggering a neural signal from the impaired body part the impaired body part being external to the brain, (b) detecting a second location of the brain in which a response neural activity occurs in reaction to the neural signal, the second location being in a second hemisphere of the brain that is contralateral to the first hemisphere, and (c) selecting the stimulation site to be at least proximate to the second location;

positioning at least a first electrode at the stimulation site; and applying an electrical potential to pass a current through the first electrode.

2. The method of claim 1 wherein triggering a neural signal comprises passively moving the body part impaired by the damage to the first location.

3. The method of claim 1 wherein triggering a neural signal comprises applying an electrical stimulation to the body part impaired by the damage to the first location.

4. The method of claim 1 wherein selecting the stimulation site further comprises detecting a third location of the brain in which a response neural activity occurs in reaction to the neural signal, the third location being in the first hemisphere.

* * * * *

UNITED STATES PATENT AND TRADEMARK OFFICE
CERTIFICATE OF CORRECTION

| | | |
|---|---|---|
| PATENT NO. | : 7,236,831 B2 | |
| APPLICATION NO. | : 10/410526 | |
| DATED | : June 26, 2007 | |
| INVENTOR(S) | : Firlik et al. | |

It is certified that error appears in the above-identified patent and that said Letters Patent is hereby corrected as shown below:

On the Title page, in Item [57], under "Abstract", in column 2, line 8, delete "If" and insert -- In --, therefor.

On Title page 3, Item [56] under "Other Publications", in column 2, line 2, after "Firlik" insert -- . --.

On Title page 4, Item [56] under "Other Publications", in column 1, line 43, delete "Potenetiation" and insert -- Potentiation --, therefor.

On Title page 4, Item [56] under "Other Publications", in column 2, line 12, delete ""Domans" and insert -- "Domains --, therefor.

On Title page 4, Item [56] under "Other Publications", in column 2, line 55, delete "imaging."" and insert -- imaging," --, therefor.

On Title page 5, Item [56] under "Other Publications", in column 1, line 5, delete "suppressess" and insert -- suppresses --, therefor.

On Title page 5, Item [56] under "Other Publications", in column 1, line 9, after "vol. 11," insert -- No. 11, --.

On Title page 5, Item [56] under "Other Publications", in column 1, line 32, delete "Friedheim" and insert -- Friedhelm --, therefor.

On Title page 5, Item [56] under "Other Publications", in column 1, line 55, delete "page.:" and insert -- page. --, therefor.

On Title page 5, Item [56] under "Other Publications", in column 2, line 32, delete "topogrpahy,"" and insert -- topography," --, therefor.

Signed and Sealed this
Seventeenth Day of May, 2011

David J. Kappos
*Director of the United States Patent and Trademark Office*

On Title page 5, Item [56] under "Other Publications", in column 2, line 47, delete "stimulation;" and insert -- stimulation: --, therefor.

On Title page 6, Item [56] under "Other Publications", in column 1, line 41, delete "Gllner." and insert -- Gliner. --, therefor.

On Title page 6, Item [56] under "Other Publications", in column 1, line 44, delete "Gilner et al." and insert -- Gliner et al. --, therefor.

On Title page 6, Item [56] under "Other Publications", in column 1, line 49, delete "on" and insert -- in --, therefor.

On Title page 6, Item [56] under "Other Publications", in column 1, line 54, delete "CNN. com," and insert -- CNN.com, --, therefor.

On Title page 6, Item [56] under "Other Publications", in column 1, line 55, delete "htt:" and insert -- http: --, therefor.

On Title page 6, Item [56] under "Other Publications", in column 2, line 7, delete "e50-e-52," and insert -- e50-e52, --, therefor.

On Title page 6, Item [56] under "Other Publications", in column 2, line 15, delete "Sterotactic" and insert -- Stereotactic --, therefor.

On Title page 6, Item [56] under "Other Publications", in column 2, line 24, delete "Qlagen" and insert -- Qiagen --, therefor.

On Title page 6, Item [56] under "Other Publications", in column 2, line 43, delete "continue" and insert -- continua --, therefor.

On Title page 6, Item [56] under "Other Publications", in column 2, line 62, delete "Som" and insert -- Some --, therefor.

On Title page 6, Item [56] under "Other Publications", in column 2, line 67, delete "Nucles;" and insert -- Nucleus: --, therefor.

On Title page 6, Item [56] under "Other Publications", in column 2, line 68, delete "control,"" and insert -- Control," --, therefor.

On Title page 6, Item [56] under "Other Publications", in column 2, line 72, delete "foci,"" and insert -- Foci," --, therefor.

On Title page 7, Item [56] under "Other Publications", in column 1, line 2, delete "intractable" and insert -- Intractable --, therefor.

CERTIFICATE OF CORRECTION (continued)
U.S. Pat. No. 7,236,831 B2

On Title page 7, Item [56] under "Other Publications", in column 1, line 5, delete "hippocampus" and insert -- Hippocampus --, therefor.

On Title page 7, Item [56] under "Other Publications", in column 1, line 7, after "Lippincott" insert -- Williams & --.

On Title page 7, Item [56] under "Other Publications", in column 1, line 10, delete "Psychiagry," and insert -- Psychiatry, --, therefor.

On Title page 7, Item [56] under "Other Publications", in column 1, line 12, delete "temproal" and insert -- temporal --, therefor.

On Title page 7, Item [56] under "Other Publications", in column 1, line 17, delete "3,asp." and insert -- 3.asp, --, therefor.

On Title page 7, Item [56] under "Other Publications", in column 1, line 20, delete "canidates," and insert -- candidates, --, therefor.

On Title page 7, Item [56] under "Other Publications", in column 2, line 3, delete "temportal" and insert -- temporal --, therefor.

In column 1, line 41–56, delete "For example, a stroke is a common condition that damages the brain. Strokes are generally caused by emboli (e.g., obstruction of a vessel), hemorrhages (e.g., rupture of a vessel), or thrombi (e.g., clotting) in the vascular system of a specific region of the brain. Such events generally result in a loss or impairment of a neural function (e.g., neural functions related to facial muscles, limbs, speech, etc.). Stroke patients are typically treated using various forms of physical therapy to rehabilitate the loss of function of a limb or another affected body part. Stroke patients may also be treated using physical therapy plus an adjunctive therapy such as amphetamine treatment. For most patients, however, such treatments are minimally effective and little can be done to improve the function of an affected body part beyond the recovery that occurs naturally without intervention." and insert the same on Col. 1, Line 40, after "difficult." as a continuation of the same paragraph.

In column 2, line 66–67, delete "ipsilaterial" and insert -- ipsilateral --, therefor.

In column 5, line 38, after "nothing"" delete ".".

In column 14, line 17, delete "of-the" and insert -- of the --, therefor.

In column 18, line 44–45, delete "20-200 ps." and insert -- 20-200 µs. --, therefor.

In column 18, lines 35–46, delete "The pulses can be a bi-phasic or monophasic stimulus that is applied to achieve a desired potential in a sufficient percentage of a population of neurons at the stimulation site. In one embodiment, the pulse form has a frequency of approximately 2–1000 Hz, but the frequency may be particularly useful in the range of approximately 40–200 Hz. For example, initial clinical trials are expected to use a frequency of approximately 50–100 Hz. The pulses can also

CERTIFICATE OF CORRECTION (continued)
U.S. Pat. No. 7,236,831 B2 have pulse widths of approximately 10 μs–100 ms, or more specifically the pulse width can be approximately 20–200 ps. For example, a pulse width of 50–100 μs may produce beneficial results." and insert the same on Col. 18, Line 33 (Approx.), after "neuroplasticity.", as the continuation of the same paragraph.

In column 24, line 37, in Claim 1, after "part" insert -- , --.